(12) United States Patent
Galliano et al.

(10) Patent No.: US 12,029,526 B2
(45) Date of Patent: Jul. 9, 2024

(54) THERAPEUTIC PELVIC REGION ANALYZER AND METHOD OF USE THEREOF

(71) Applicants: Domingo E. Galliano, Port Charlotte, FL (US); Kathleen Lueck, Port Charlotte, FL (US); Christopher Ross, Davie, FL (US); Thomas Fernandez, Miramar, FL (US)

(72) Inventors: Domingo E. Galliano, Port Charlotte, FL (US); Kathleen Lueck, Port Charlotte, FL (US); Christopher Ross, Davie, FL (US); Thomas Fernandez, Miramar, FL (US)

( * ) Notice: Subject to any disclaimer, the term of this patent is extended or adjusted under 35 U.S.C. 154(b) by 853 days.

(21) Appl. No.: 16/699,399

(22) Filed: Nov. 29, 2019

(65) Prior Publication Data

US 2020/0178806 A1    Jun. 11, 2020

Related U.S. Application Data

(63) Continuation-in-part of application No. 14/873,780, filed on Oct. 2, 2015, now abandoned, which is a continuation-in-part of application No. 13/399,906, filed on Feb. 17, 2012, now abandoned.

(60) Provisional application No. 61/443,759, filed on Feb. 17, 2011.

(51) Int. Cl.
*A61B 5/00* (2006.01)
*A61B 5/11* (2006.01)
*A61B 5/20* (2006.01)
*A61B 5/22* (2006.01)

(52) U.S. Cl.
CPC .......... *A61B 5/0053* (2013.01); *A61B 5/1107* (2013.01); *A61B 5/202* (2013.01); *A61B 5/227* (2013.01); *A61B 5/486* (2013.01); *A61B 5/6846* (2013.01)

(58) Field of Classification Search
None
See application file for complete search history.

(56) References Cited

U.S. PATENT DOCUMENTS 4,050,449 A * 9/1977 Castellana ............. A61B 5/227
600/38
5,236,423 A * 8/1993 Mix .................... A61M 25/0111
600/920
6,606,907 B1 * 8/2003 Rosendahl ......... A63B 21/0085
73/379.01

(Continued)

*Primary Examiner* — Matthew Kremer
(74) *Attorney, Agent, or Firm* — The Concept Law Group, PA; Scott D. Smiley; Scott M. Garrett

(57) ABSTRACT

A therapeutic pelvic region analyzer and method of use thereof that includes an expandable device sized and shaped for insertion into an opening in a pelvic region of a user and a collapsible reservoir fluidly coupled to the expandable device. The collapsible reservoir is configured to temporarily retain and expel an amount of fluid. A tube defining a fluid-flow path for the amount of fluid is between the expandable device and the collapsible reservoir. The therapeutic pelvic region analyzer also includes fluid-flow control valve disposed between the expandable device and the collapsible reservoir. The fluid-flow control valve is operable to provide a selectively variable level of resistance as the amount fluid passes from the expandable device to the collapsible reservoir.

3 Claims, 28 Drawing Sheets

(56) References Cited

U.S. PATENT DOCUMENTS

2016/0287163 A1\* 10/2016 Golden ............... A61B 5/1076

\* cited by examiner

Recto-anal inhibitory reflex describes the relaxation of the internal anal sphincter in response to distention of the rectum.

If RAIR is present (normal)

The graph meter will record

2405

If RAIR is not present (abnormal)

The graph meter will record

2410

THERAPEUTIC PELVIC REGION ANALYZER AND METHOD OF USE THEREOF

CROSS-REFERENCE TO RELATED APPLICATION

This application is a continuation-in-part application and claims priority to U.S. application Ser. No. 14/873,780, filed Oct. 2, 2015, which was a continuation-in-part application of U.S. application Ser. No. 13/399,906, filed on Feb. 17, 2012, which claims priority to U.S. Provisional Application No. 61/443,759, filed on Feb. 17, 2011; the entireties of these applications are incorporated by reference.

STATEMENT REGARDING FEDERALLY SPONSORED RESEARCH OR DEVELOPMENT

Not Applicable.

FIELD OF THE INVENTION

The present disclosure lies in the field of pelvic floor dysfunction and, particularly, relates to methods and devices for providing pelvic floor dysfunction therapeutics and diagnostics by measuring a flow rate at which a fluid is moved by a patient upon contracting muscles affected by pelvic floor dysfunction against a reservoir.

BACKGROUND OF THE INVENTION

Pelvic floor dysfunction, e.g., urinary or anal incontinence, constipation, and pelvic pain, may be treated by medical professionals or therapists with the use of pelvic rehabilitation. Pelvic rehabilitation is the use of electrical stimulation to increase the muscle awareness, recruitment, strength, tone, and endurance of targeted muscles in the pelvic region.

In one type of pelvic rehabilitation program, patients are given six weeks therapy of anal electrical stimulation and weekly education on a prescribed exercise program to be performed daily in the patients' homes. The prescribed exercise program includes contracting the targeted muscle(s) for a first predetermined amount of time and relaxing the targeted muscle(s) for a second predetermined amount of time. This exercise (or cycle) is normally performed a predetermined number of times in a row and repeated a predetermined number of times each day.

Fifty percent of the treatment success is due to patient participation. The patient needs to identify the correct muscle(s), squeeze the muscle, hold the muscle, and then relax the muscle. When patients are with the therapist, they are able to successfully perform the exercises through constant education and monitoring. However, when patients are in between treatments while at home, they may perform the exercise improperly and not in accordance with the proper technique learned in the therapy sessions. The patients' muscle may become weak and it will become even harder for them to identify the proper muscle, thereby making it impossible to do the exercises correctly.

FIG. 1 illustrates a side view of the rectum and anus, which are sections of the lower gastrointestinal tract. Various muscles, muscle layers, and other layers of the rectum and anus are shown, e.g. the mucosa, the Levator Ani muscle, fatty tissue, the Puborectalis muscle, and the Dentate line. The internal sphincter and external sphincter of the anus are the muscles that targeted to treat anal incontinence, a certain type of pelvic floor dysfunction.

Usually, diagnoses, and treatments, of anal incontinence are performed with a medical professional using an anorectal manometry device. Anorectal manometry devices are very expensive; they can cost upwards of $40,000. Because it is a very expensive device for a medical professional to purchase, it is even more impractical for a patient to have the anorectal manometry device in their home. In addition, Solesta® is a gel that is used to treat anal incontinence but is only prescribed by doctors after a proper diagnosis of a patient has been obtained using the expensive prior art anorectal manometry device. It would be desirable to eliminate the need to diagnose such conditions without using the expensive prior art anorectal manometry device.

Thus, a need exists to overcome the problems with the prior art systems, designs, and processes as discussed above.

SUMMARY OF THE INVENTION

In accordance with some embodiments of the inventive disclosure, there is provided a therapeutic pelvic region analyzer that include an expandable device sized and shaped for insertion into an opening in a pelvic region of a user and a collapsible reservoir fluidly coupled to the expandable device and configured to temporarily retain and expel an amount of fluid. The analyzer can further include a tube defining a fluid-flow path for the amount of fluid between the expandable device and the collapsible reservoir, and a fluid-flow control valve disposed between the expandable device and the collapsible reservoir and operable to provide a selectively variable level of resistance as the amount of fluid passes from the expandable device to the collapsible reservoir. The analyzer can further include a fluid flow rate reading device coupled to the fluid-flow control valve and which is operable to measure a fluid flow rate between the collapsible reservoir and the expandable device as a result of force exerted by a user against a selected level of resistance provided by the fluid-flow control valve. The fluid-flow control valve is coupled to the fluid flow rate reading device through a fluid flow rate port disposed on the fluid-flow control valve.

In accordance with a further feature, the expandable device is made of a non-elastic material.

In accordance with a further feature, the expandable device is a distention bag.

In accordance with a further feature, the collapsible reservoir is a fluid dispensing bulb having a reservoir body made of a pliable material.

In accordance with a further feature, the amount of fluid is a quantity of water.

In accordance with a further feature, the analyzer further include a stop member coupled to the expandable device, the stop member including a width larger than a width of the expandable device.

In accordance with a further feature, the expandable device, the collapsible reservoir, and the tube form a fluid flow tolerant sealed system.

In accordance with some embodiments of the inventive disclosure, there is provided a therapeutic pelvic region analyzer that includes an expandable device sized and shaped for insertion into an opening in a pelvic region of a user, and a reservoir fluidly coupled to the expandable device and configured to retain and expel an amount of fluid. The analyzer can further include a tube defining a fluid-flow path for the amount of fluid between the expandable device and the reservoir, and a fluid-flow control valve disposed between the expandable device and the reservoir and operable to provide a selectively variable level of resistance as the amount of fluid passes from the expandable device to the reservoir. The analyzer can further include a fluid flow rate reading device coupled to the fluid-flow control valve and operable to measure a fluid flow rate between the reservoir and the expandable device as a result of force exerted by a user against a selected level of resistance provided by the fluid-flow control valve.

In accordance with a further feature, the expandable device is a foldable distention bag.

In accordance with a further feature, the reservoir includes a squeezable body sized and shaped to fit within a palm of a user's hand.

In accordance with a further feature, the expandable device, the reservoir, and the tube form a fluid tolerant sealed system.

In accordance with a further feature, the fluid flow rate reading device is coupled to the fluid-flow control valve through a fluid flow rate port disposed on the fluid-flow control valve.

In accordance with a further feature, the fluid flow rate reading device is operably configured to provide an indication of a muscle squeeze strength of the user in response to the selected level of resistance provided by the fluid-flow control valve, and provide an indication of a muscle endurance in response to the selected level of resistance provided by the fluid-flow control valve.

In accordance with a further feature, the amount of fluid is a quantity of water.

In accordance with some embodiments of the inventive disclosure, there is provided a method for providing pelvic region therapy. The method can include providing a therapeutic pelvic region analyzer that includes an expandable device sized and shaped for insertion into an opening in a pelvic region of a user, a reservoir fluidly coupled to the expandable device and configured to temporarily retain and expel an amount of fluid, a tube defining a fluid-flow path for the amount of fluid between the expandable device and the reservoir, and a fluid-flow control valve disposed between the expandable device and the reservoir and operable to provide a selectively variable level of resistance as the amount of fluid passes from the expandable device to the reservoir. The method can further include providing a fluid flow rate reading device coupled to the fluid-flow control valve, the fluid flow rate reading device operable to measure a flow rate of fluid moved between the reservoir and the expandable device, inserting the expandable device in the pelvic region of the user, and instructing the user to contract the pelvic region to expel the amount of fluid from the expandable device in a direction to the reservoir. The method can further include measuring the flow rate of fluid moved from the expandable device to the reservoir as a result of the user contracting the pelvic region.

In accordance with a further feature, the method can further include adjusting the fluid-flow control valve to provide a select level of resistance as the amount of fluid passes from the expandable device to the reservoir.

In accordance with a further feature, the method can further include providing a fluid flow rate reading device coupled to the fluid-flow control valve, the fluid flow rate reading device operable to measure a force exerted by the user in response to a selected level of resistance provided by the fluid-flow control valve.

In accordance with a further feature, the method can further include repeating the step of expelling the amount of fluid from the reservoir to the expandable device along the fluid-flow path to provide pelvic region therapy to the user.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and explain various principles and advantages all in accordance with the present disclosure. Advantages of embodiments of the present disclosure will be apparent from the following description of the exemplary embodiments thereof, which description should be considered in conjunction with the accompanying drawings in which.

DETAILED DESCRIPTION

Figure 1:
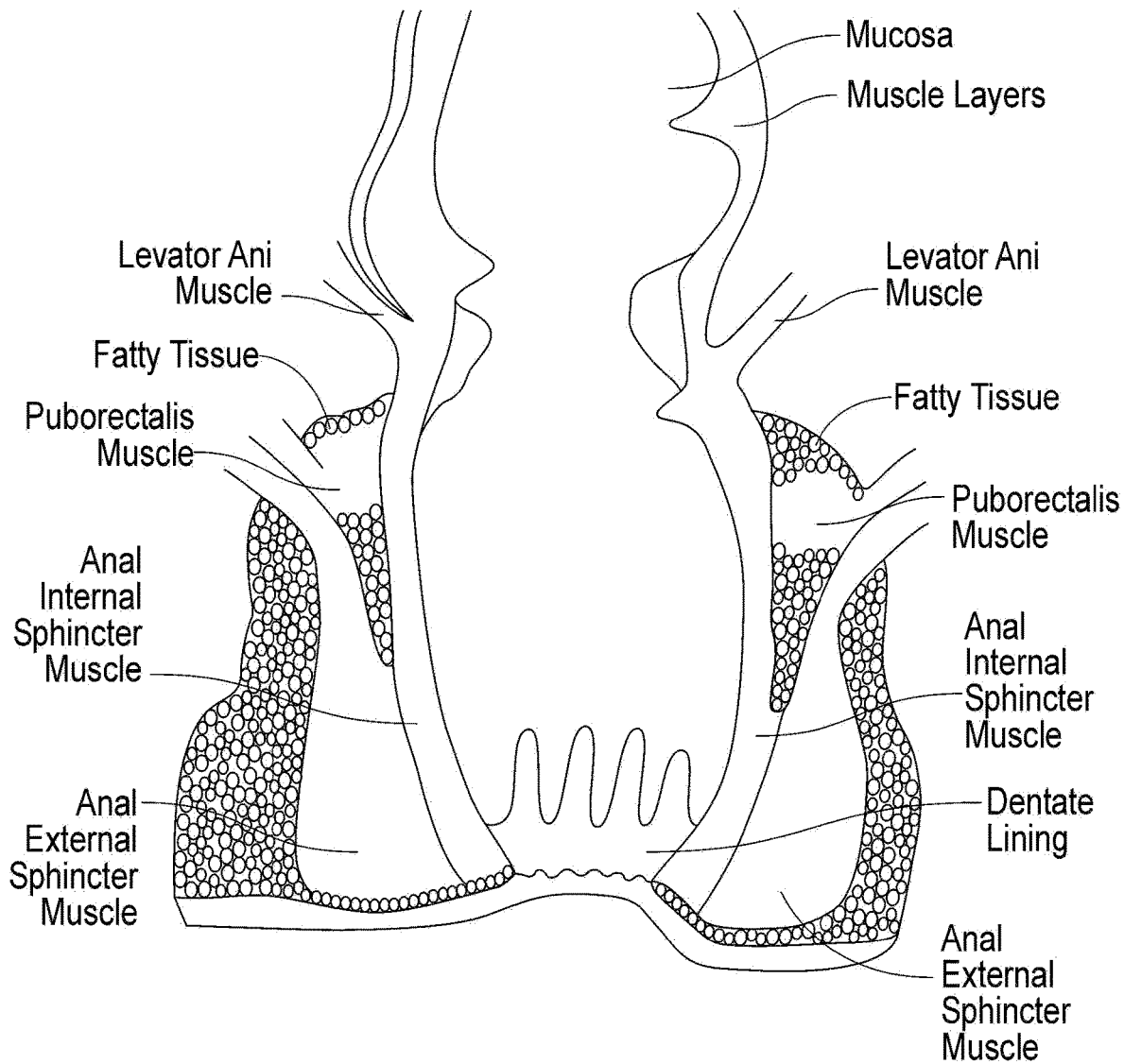
FIG. 1 is a cross-sectional view of an anus, rectum, and associated internal and external sphincter muscles.

As required, detailed embodiments of the present disclosure are disclosed herein; however, it is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting; but rather, to provide an understandable description of the disclosure. While the specification concludes with claims defining the features of the disclosure that are regarded as novel, it is believed that the disclosure will be better understood from a consideration of the following description in conjunction with the drawing figures, in which like reference numerals are carried forward.

Alternate embodiments may be devised without departing from the spirit or the scope of the disclosure. Additionally, well-known elements of exemplary embodiments of the disclosure will not be described in detail or will be omitted so as not to obscure the relevant details of the disclosure.

Before the present disclosure is disclosed and described, it is to be understood that the terminology used herein is for the purpose of describing particular embodiments only and is not intended to be limiting. The terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically.

Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a nonexclusive inclusion, such that a process, method, article, or apparatus that comprises a list of elements does not include only those elements but may include other elements not expressly listed or inherent to such process, method, article, or apparatus. An element proceeded by "comprises . . . a" does not, without 14 more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure.

The terms "program," "software," "software application," and the like as used herein, are defined as a sequence of instructions designed for execution on a computer system. A "program," "software," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

Herein various embodiments of the present disclosure are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Figure 2:
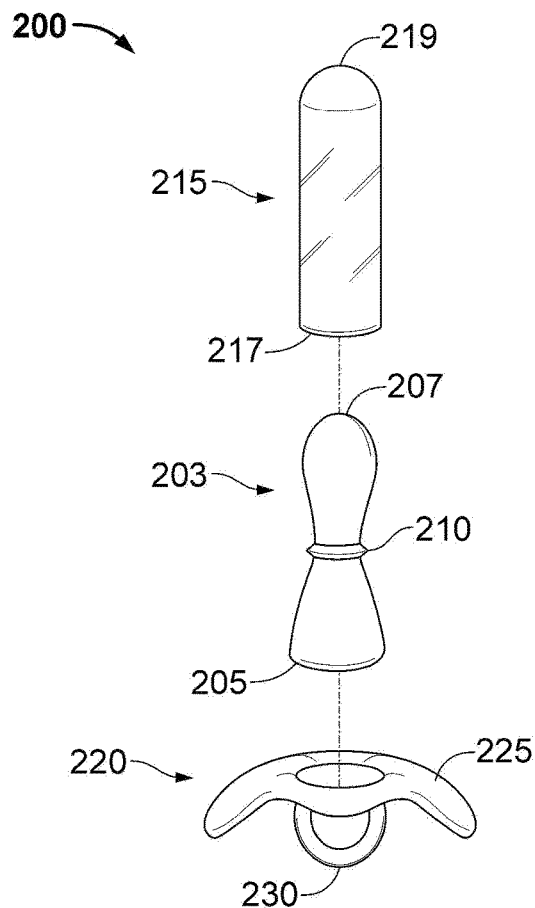
FIG. 2 is an exploded perspective view of an exemplary embodiment of a probe, sensor, cover, and base of an analyzer.
Figure 3:
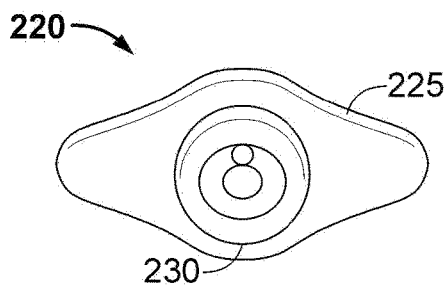
FIG. 3 is a bottom plan view of the base of FIG. 2.

Described now are exemplary embodiments of the present disclosure. Referring now to the figures of the drawings in detail and first, particularly to FIG. 2, there is shown a first exemplary embodiment of an analyzer 200 of the present invention with the parts separated from one another. The analyzer 200 comprises a probe 203, a cover 215, and a base 220. The probe 203 has a proximal end 205 and a distal end 207. In this exemplary embodiment, the sensor 210 is disposed at an intermediate portion of probe 203, e.g., at a midpoint thereof, and is integrated with probe 203. The base 220 may be attached to the proximal end 205 of the probe 203 or, if desired, it can be fixed thereto. The base 220 has a flap 225 and a grasper 230. In an exemplary embodiment, the probe 203 is of hard plastic, such as, for example, polyethylene, polypropylene, polystyrene, polyvinyl chloride, and polytetrafluoroethylene (PTFE). The grasper 230 may be a ring, knob, or other handle that allows a user of the analyzer 200 to insert and remove the analyzer from a desired area of the user's pelvic floor region. In an exemplary embodiment, the desired pelvic floor region can be anal or vaginal. The base 220 can be of soft rubber or latex for comfort of a user FIG. 3 shows a view from the bottom of the base 220 with its flap 225 and grasper 230, in the form of a ring. Returning to FIG. 2, the cover 215 has a proximal end 217 and a distal end 219. The cover 215 may be placed over the probe 203 and the sensor 210. The cover 215 may be any soft material capable of keeping bodily fluids away from the sensor 210 and the probe 203. In one exemplary embodiment, cover 215 is soft rubber or latex or silicone, which allows for easier insertion and comfort as well.

Figure 4:
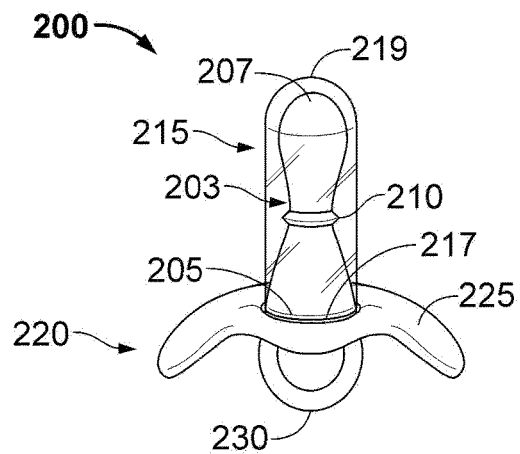
FIG. 4 is a perspective view from the side of the analyzer of FIG. 2.

FIG. 4 illustrates a side view of the exemplary embodiment of the analyzer 200. In this view, the analyzer 200 can be said to be shaped similar to a baby's pacifier. For assembly, the cover 215 is placed over the probe 203 and the sensor 210, and is sized to either snugly or loosely fit the probe 203 therein. Then, the proximal end 205 of the probe 203 is attached to the base 220 to clamp fix the cover 215 there between until the base 220 is removed. In the exemplary embodiment, the probe 203 and the cover 215 are fixedly attached to the base 220. Analyzer 200 may be used in conjunction with an outer covering or sleeve (similar to a thin covering used by doctors to cover thermometers so that the thermometer may be reused without having to sanitize). Analyzer 200 may also be used without such an outer sleeve; in which case it must be sanitized according to accepted medical practice and procedures.

In use for the anus, for example, the distal end 207 of the probe 203 is inserted into the rectum. The sensor 210 receives indication of a muscle squeeze, i.e., squeezing of the internal and/or external sphincter as the rectum tightens on the distal end 207. The analyzer 200 emits a sound that indicates strength of the muscle squeeze. In one exemplary embodiment, a volume of the sound increases in accordance with the strength, e.g., flow rate resulting from, the exertion of the muscle(s) on the sensor 210. Alternatively, or additionally, a frequency of the sound is changed (upwards or downwards) dependent upon the amount of force exerted upon the probe 203. A duration of the sound, i.e., the time that the force is imparted corresponding to a contraction of the muscle, indicates endurance of the exercise. Muscle squeezes by a user having a strength and endurance meeting a threshold are indicated by the analyzer 200 to the user to be "successful." Success may be indicated to the user audibly, visually, or via the use of a vibrator.

Figure 5:
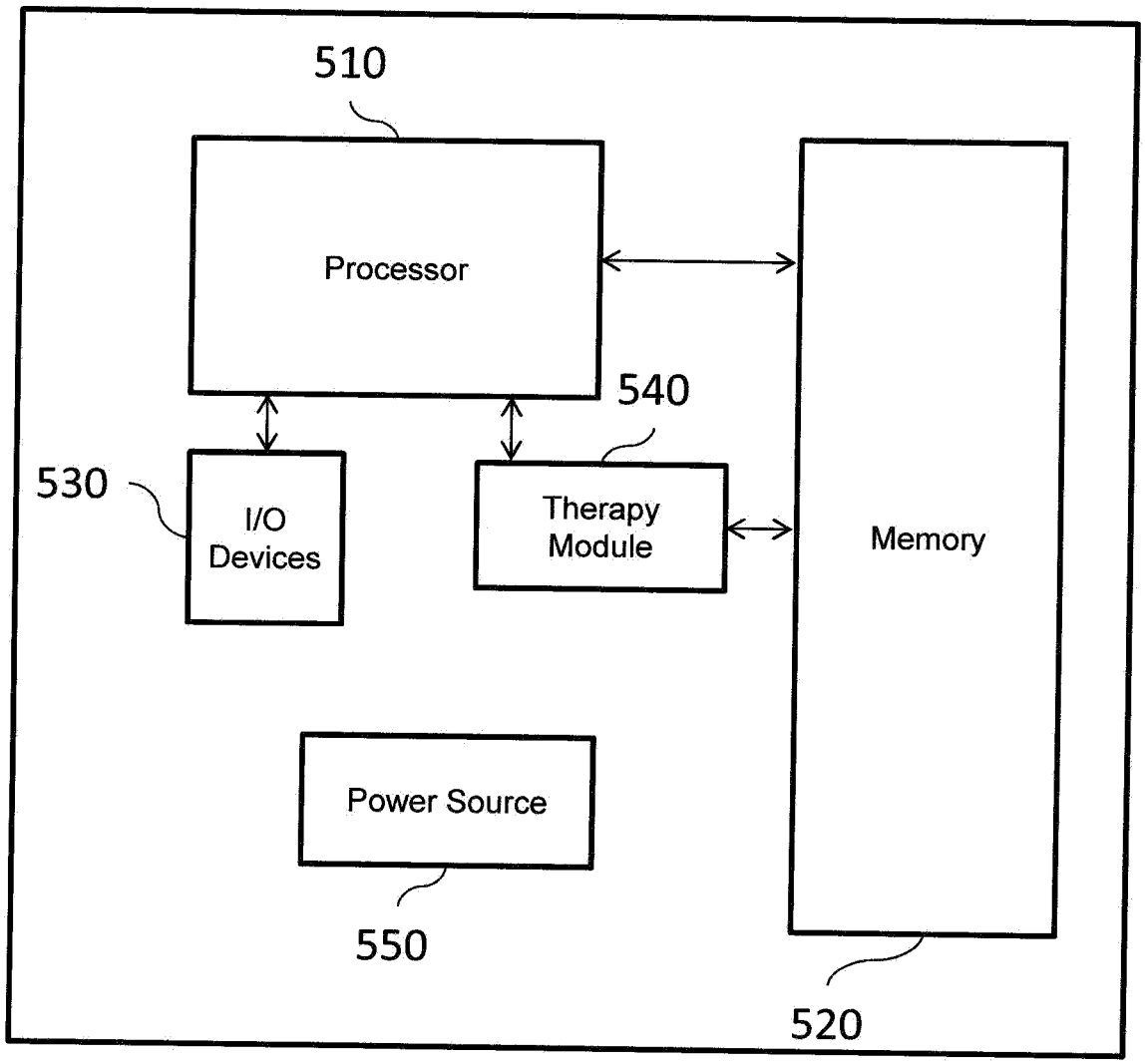
FIG. 5 is a block circuit diagram of an exemplary embodiment of a diagnostic device according to the invention.

FIG. 5 is a block circuit diagram of an example device 500 for performing diagnostic tests according to the invention. Specifically, the device 500 can be employed to provide personal pelvic floor rehabilitation therapy and, therefore, may be implemented in the analyzer 200. The device 500 comprises a processor (CPU) 510, a memory 520 (e.g., random access memory (RAM) and/or read only memory (ROM)), a therapy module 540, a power source 550, and various input/output devices 530 (for example, a sensor (e.g., sensor 210), a light source operating as a visual indicator, and an indicator operating using vibration). The power source 550 may be alternating current (AC) or a battery. In one embodiment, the analyzer 200, 500 is a portable, handheld device having a rechargeable power source 550.

It should be understood that therapy module 540 can be implemented as one or more physical devices that are coupled to the CPU 510 through a communication channel. Alternatively, therapy module 540 can be represented by one or more software applications (or even a combination of software and hardware, e.g., using application specific integrated circuits (ASIC)), where the software is loaded from a storage medium, (e.g., a magnetic or optical drive or diskette) and operated by the CPU in the memory 520 of the computer. As such, therapy module 540 (including associated data structures) of the present disclosure can be stored on a non-transitory computer readable medium, e.g., RAM memory, magnetic or optical drive or diskette and the like.

Figure 6:
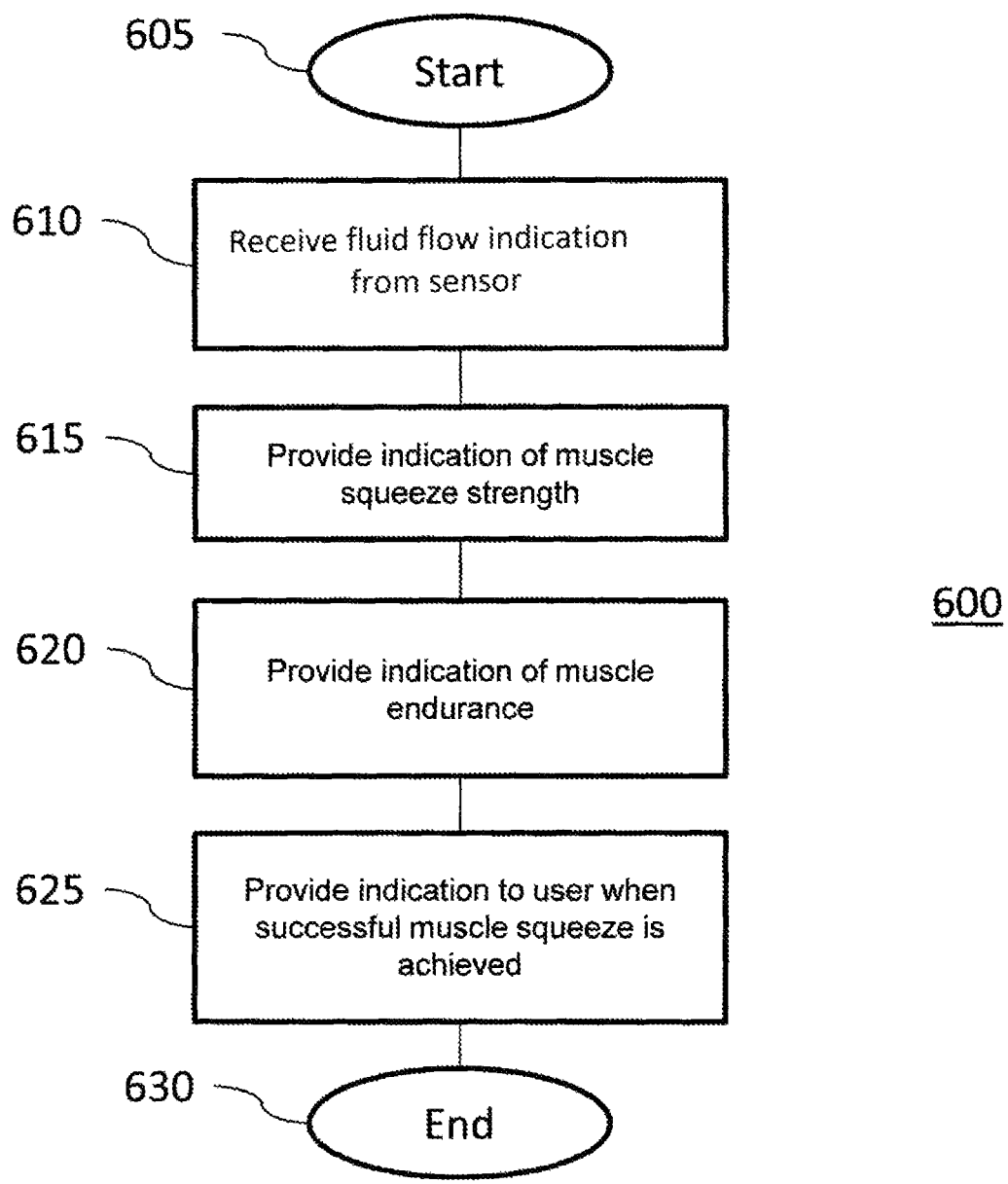
FIG. 6 is a flow chart illustrating an exemplary embodiment of a method for providing personal pelvic floor dysfunction therapy according to the invention.

FIG. 6 illustrates a method 600 for providing personal pelvic floor dysfunction therapy according to one exemplary embodiment of the invention. Method 600 may be implemented in analyzer 200, 500. Method 600 starts at step 605 and proceeds to step 610, where a flow rate indication is received from a sensor, e.g. sensor 210. At step 615, an indication of muscle squeeze strength is provided. In one embodiment, the indication of muscle squeeze strength is any or both of a volume or a frequency of a sound. For example, the volume of the sound increases in accordance with the strength of the muscle squeeze. At step 620, an indication of muscle endurance is provided. In one exemplary embodiment, the indication of muscle endurance is a length of time that the sound lasts, corresponding to a held muscle squeeze exerting an amount of flow volume. At step 625, an indication is provided when a successful muscle squeeze is achieved. The successful muscle squeeze indication may be provided aurally, visually, or through a vibrator indicator. Method 600 ends at step 630.

Figure 7:
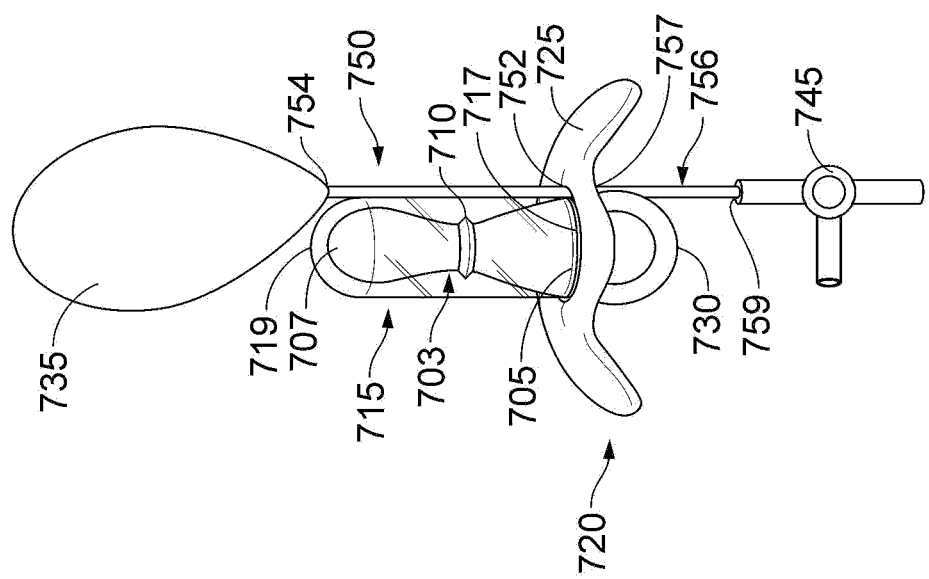
FIG. 7 is a perspective view from the side of another exemplary embodiment of an analyzer according to the invention.

FIG. 7 illustrates another exemplary embodiment of an analyzer 700 of the present invention, which comprises a probe 703, a cover 715, a base 720, a balloon 735, a flow rate and volume reading window 740, a valve 745 (FIG. 8), a main fluid tube 756, and a secondary fluid tube 750. The probe 703 has a proximal end 705 and a distal end 707. This embodiment can serve as a device to perform a handheld, anal/rectal manometry/rectal sensation tone and compliance test. As is known, anal/rectal manometry measures the force of the anal sphincter for constipation and/or anal incontinence due to carious disorders. This device is used, for example, as a diagnostic tool for patients with such constipation and/or anal incontinence.

In this exemplary embodiment, the sensor 710 is disposed at an intermediate portion of probe 203, e.g., at a midpoint thereof, and is integrated with the probe 703. The base 720 may be attached to the proximal end 705 of the probe 703 or, if desired, it can be fixed thereto. The base 720 has a flap 725 and a grasper 730. In an exemplary embodiment, the probe 203 is of hard plastic, such as, for example, polyethylene, polypropylene, polystyrene, polyvinyl chloride, and polytetrafluoroethylene (PTFE). The grasper 730 may be a ring, knob, or other handle that allows a user of the analyzer 700 to insert and remove the analyzer from a desired area of the user's pelvic floor region. In an exemplary embodiment, the desired pelvic floor region can be anal or vaginal. The base 720 can be of soft rubber or latex or silicone for comfort of a user.

The cover 715 has a proximal end 717 and a distal end 719. The cover 715 may be placed over probe 703 and sensor 710. The cover 715 may be any soft material capable of keeping bodily fluids away from the sensor 710 and the probe 703. In one exemplary embodiment, the cover 715 is soft rubber or latex, which allows for easier insertion and comfort as well.

The analyzer 700 can be said to be shaped similar to a baby's pacifier. For assembly, the cover 715 is places over the probe 703 and the sensor 710, and is sized to either snugly or loosely fit the probe 703 therein. Then, the proximal end 705 of the probe 703 is attached to base 720 to clamp fix the cover 715 there between until the base 720 is removed.

Also provided is a balloon assembly. The secondary fluid tube 750 of the balloon assembly has a proximal end 752 and a distal end 754. The secondary fluid tube 750 is placed alongside the cover 715 and runs to a bifurcated joint 765 (see FIG. 8) at flap 725 of base 720. The distal end 754 of the secondary fluid tube 750 is attached to the balloon 735.

In one exemplary embodiment, the balloon 735, when inflated is extended six inches above the distal end 719 of the cover 715. In one exemplary embodiment, the probe 703 and the cover 715 are fixedly attached to base 720. Analyzer 700 may be used in conjunction with an outer covering or sleeve (similar to a thin covering used by doctors to cover thermometers so that the thermometer may be reused without having to sanitize). Analyzer 700 may also be used without such an outer covering, in which case, it must be sanitized according to accepted medical practices and procedures.

Figure 8:
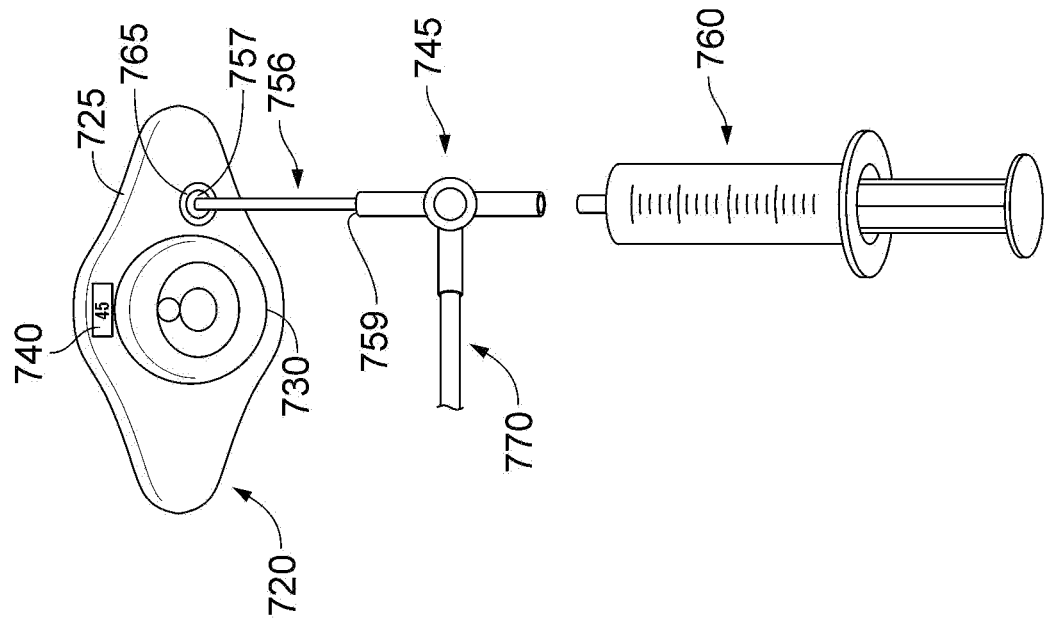
FIG. 8 is a bottom perspective and partially exploded view of a base, a main fluid tube, a bifurcated joint, and a valve of the analyzer of FIG. 7.

Viewed from the bottom of the base 720, FIG. 8 shows a mam fluid tube 756, a bifurcated joint 765, and a valve 745. The proximal end 752 (see FIG. 7) of the secondary fluid tube 750 is attached to the bifurcated joint 765. A distal end 757 of the main fluid tube 756 is attached to the bifurcated joint 765 at the flap 725. A proximal end 759 of the main fluid tube 756 is attached to the valve 745, which is used to prevent fluid from expelling out from balloon 735 until desired. In one exemplary embodiment, the valve 745 is a luer-lock, two-way valve with the main fluid tube 756 attached to the valve 745. In one exemplary embodiment, the valve 745 may have a sensor 770 that measures flow rate from the balloon 735. In another exemplary embodiment, the valve 745 may also be attached to a tube 770 (which is coupled to an external device) that is used to measure flow rate from balloon 735.

The base 720 includes a Flow rate and flow volume reading window 740, which may be integrated in the flap 725 or the grasper 730, for example, in a case where the grasper 730 is a knob or any other solidly shaped object allowing for placement of the flow rate reading window. In one exemplary embodiment, the fluid flow rate reading window 740 is a digital fluid flow rate reading window. The flow rate reading window 740 is electronically coupled (coupling not shown) to sensor 710 and provides flow information from the sensor 710 to the flow rate reading window 740.

During an exemplary diagnostic test according to the invention, the analyzer 700, including the balloon 735, is inserted into the pelvic floor region of the patient. In one exemplary embodiment, a distal end of the analyzer 700 (e.g., distal ends 707, 719) is inserted into the rectum of a patient until the flap 725 of the analyzer 700 abuts the anus of the patient. Fluid is caused to enter the balloon 735 (e.g., using a syringe 760) through the valve 745. The pressurized fluid fills the balloon 735 through the main 756 and secondary 750 tubes Diagnostic tests (as described below with respect to FIGS. 10, 11, and 12) may be performed on the patient by a medical professional using responses from the patient and readings from flow rate reading window 740. These tests may be performed when the balloon 735 is empty, as the balloon 735 fills with fluid, or as fluid is released from the balloon 735, as set forth in accordance with the diagnostic tests.

Figure 9:
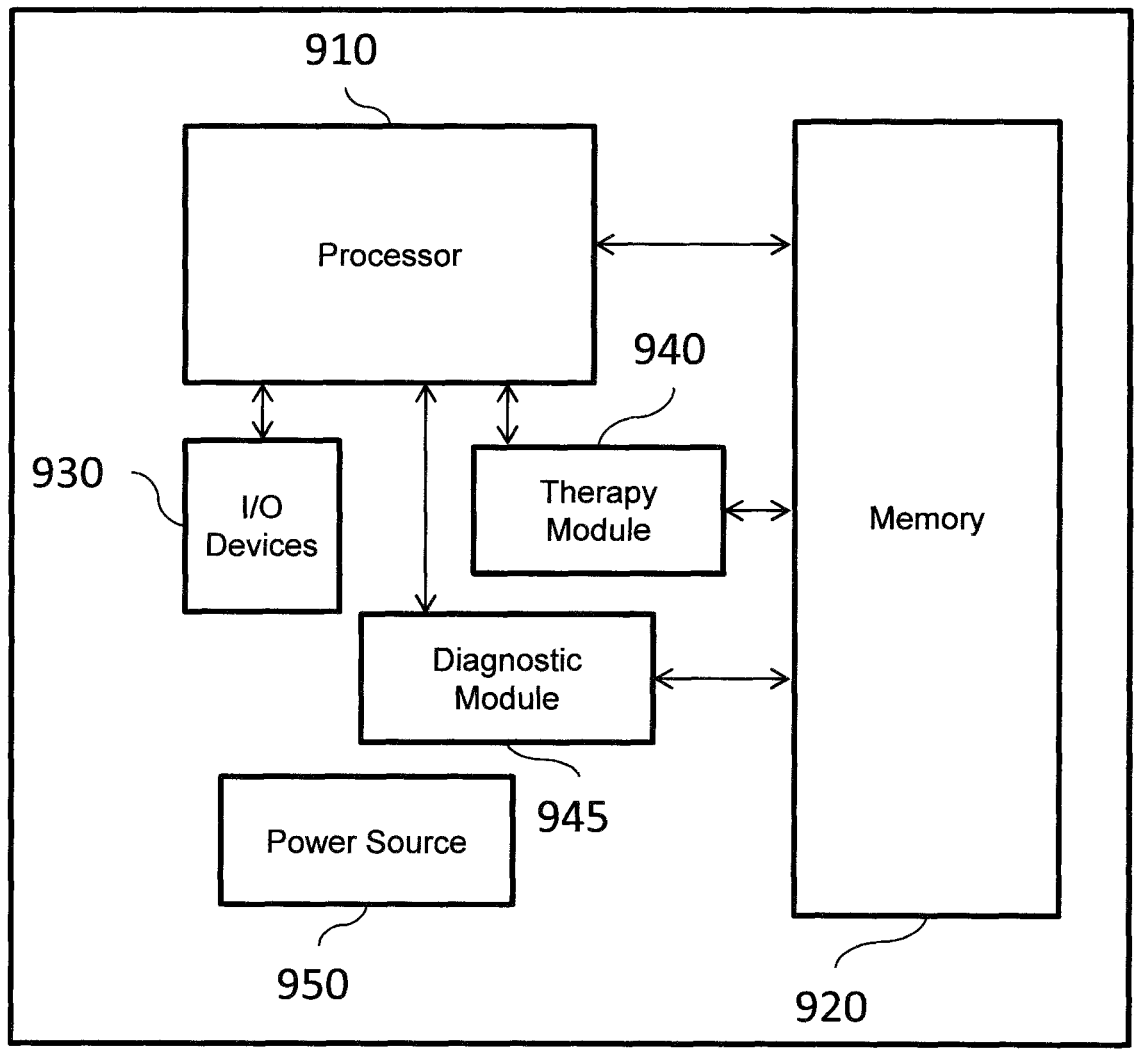
FIG. 9 is a block circuit diagram of another exemplary embodiment of an analyzer according to the invention.

FIG. 9 is a block circuit diagram of an example device 900 for performing diagnostic tests according to the invention. Specifically, the device 900 can be employed to provide pelvic floor rehabilitation therapy and diagnostics and, therefore, may be implemented in the analyzer 700. The device 900 comprises a processor (CPU) 910, a memory 920 (e.g., a random access memory (RAM) and/or read only memory (ROM)), a therapy module 940, a diagnostic module 945, a power source 950, and various input/output devices 930 including, for example, a sensor (e.g., sensor 710), a light source operating as a visual indicator, an indicator operating using vibration, storage devices, including but not limited to, a tape drive, a floppy drive, a hard disk drive or a compact disk drive, a receiver, a transmitter, a Universal Serial Bus (USB) mass storage, a network attached storage, and/or a storage device on a network cloud).

A receiver 930 and a transmitter 930 (e.g., transceiver) may be used for short-range wireless protocol communication, e.g. WI-FI®, BLUETOOTH®. The device 700, 900 may communicate with a smart phone, a tablet, or another computing device via the short-range wireless protocol in order to provide data from the device 700, 900 to a diagnostic application residing on the smart phone, tablet, or computing device. Likewise, the device 700, 900 may communicate with a smart phone, tablet, or other computing device using a USB connection. Data may be provided from device 700, 900 to the diagnostic application residing on the smart phone, tablet, or other computing device using the USB connection. The power source 950 may be alternating current (AC) or a battery. In one exemplary embodiment, the analyzer 700, 900 is a portable, handheld device having a rechargeable power source 950.

It should be understood that therapy module 940 and diagnostic module 945 can be implemented as one or more physical devices that are coupled to the CPU 910 through a communication channel. Alternatively, therapy module 940 and diagnostic module 945 can be represented by one or more software applications (or even a combination of software and hardware, e.g., using application specific integrated circuits (ASIC)), where the software is loaded from a storage medium, (e.g., a magnetic or optical drive or diskette) and operated by the CPU in the memory 920 of the computer. As such, therapy module 940 and diagnostic module 945 (including associated data structures) of the present disclosure can be stored on a non-transitory computer readable medium, e.g., RAM memory, magnetic or optical drive or diskette and the like.

Figure 10:
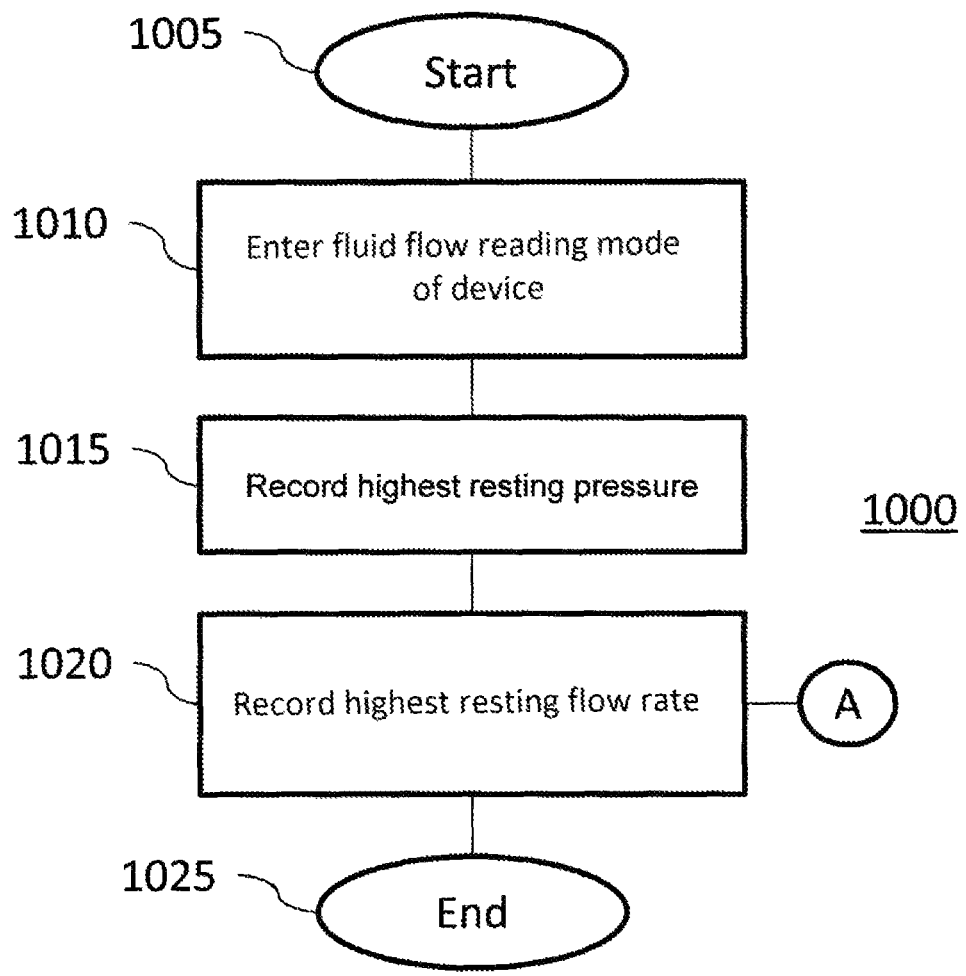
FIG. 10 is a flow chart of a method for providing rectal sensation compliance diagnostics, according to one embodiment.

FIG. 10 illustrates a diagram of a method 1000 according to one exemplary embodiment of the invention. Method 1000 comprises an anal manometry diagnostic test for performance by a device, e.g., device 700, 900. Method 1000 begins at step 1005. A patient is placed in a left lateral position. Spine alignment is not needed when using the analyzer 700, 900. The analyzer 700, 900 is lubricated and inserted into the rectum to a 6 cm marking of secondary tube 750 at the anal verge. As a frame of reference, the balloon 735 is located at a 1 cm marking on the secondary tube 750. While looking at the analyzer display screen 740 (whether on the base 220, 720 or on a separate, device communicating with the sensor 210, 710, for example, in FIGS. 13, 16, 19, and 21), a diagnostician using the device slowly moves the analyzer back and forth from the 6 cm mark to a 2 cm marker at the anal verge to find and record both the resting and highest flow rate. Typically, the highest resting flow rate is found when the marker of secondary tube 750 is between 3 cm and 4 cm inferior of the anal verge. At step 1010, a flow rate reading mode of the device is entered. Flow rate readings may be read from display screen 740, whether on the base 220, 720 or on the separate device. The patient rests quietly with no squeezing or straining for 20-30 seconds while a resting flow rate is recorded at step 1015. Resting flow rate approximates the internal anal sphincter muscle. At step 1020, a highest squeeze flow rate is recorded. The patient is instructed to squeeze as hard as possible for 5 seconds. The maximum squeeze flow rate and flow volume are then recorded. Maximum squeeze flow rate approximates the external anal sphincter muscle. Method 1000 either ends at step 1025, or proceeds to step 1110 of FIG. 11.

Figure 11:
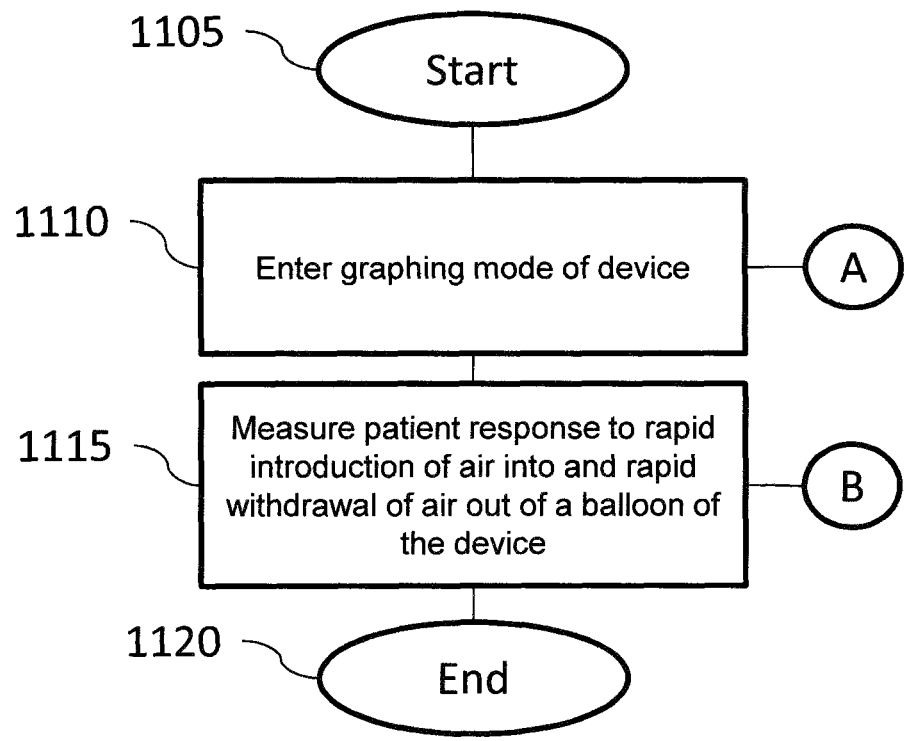
FIG. 11 is a flow chart of a method for providing anal monometry diagnostics, according to one embodiment.

FIG. 11 illustrates a diagram of a method 1100 according to another exemplary embodiment of the invention. Method 1100 comprises a Recto-Anal Inhibitory Reflex (RAIR) diagnostic test performed by device 700, 900. Method 1100 either starts at step 1105 or is initiated after a user proceeds from step 1020 to step 1110. At step 1110, a graphing mode of the device is entered. Device 700, 900 should be within the rectum at the high resting flow rate zone of the patient, e.g., where the marker of secondary tube 750 is about 3 cm to 4 cm inferior of the anal verge. At step 1115, a patient response to rapid introduction of fluid into and rapid withdrawal of fluid out from the balloon 735 is measured. Using an inflation device, e.g., syringe 760, 40 cc to 60 cc of fluid is abruptly plunged into balloon 735 and, within 2 to 4 seconds thereafter, the fluid is completely withdrawn from the balloon to identify whether RAIR is present. When balloon 735 is rapidly inflated, a normal patient will exhibit a particular reflex. Absence of such a reflex is a clear indication of Hirschsprung's disease. Method 1100 either ends at step 1120, or proceeds to step 1210 of FIG. 12.

Figure 12:
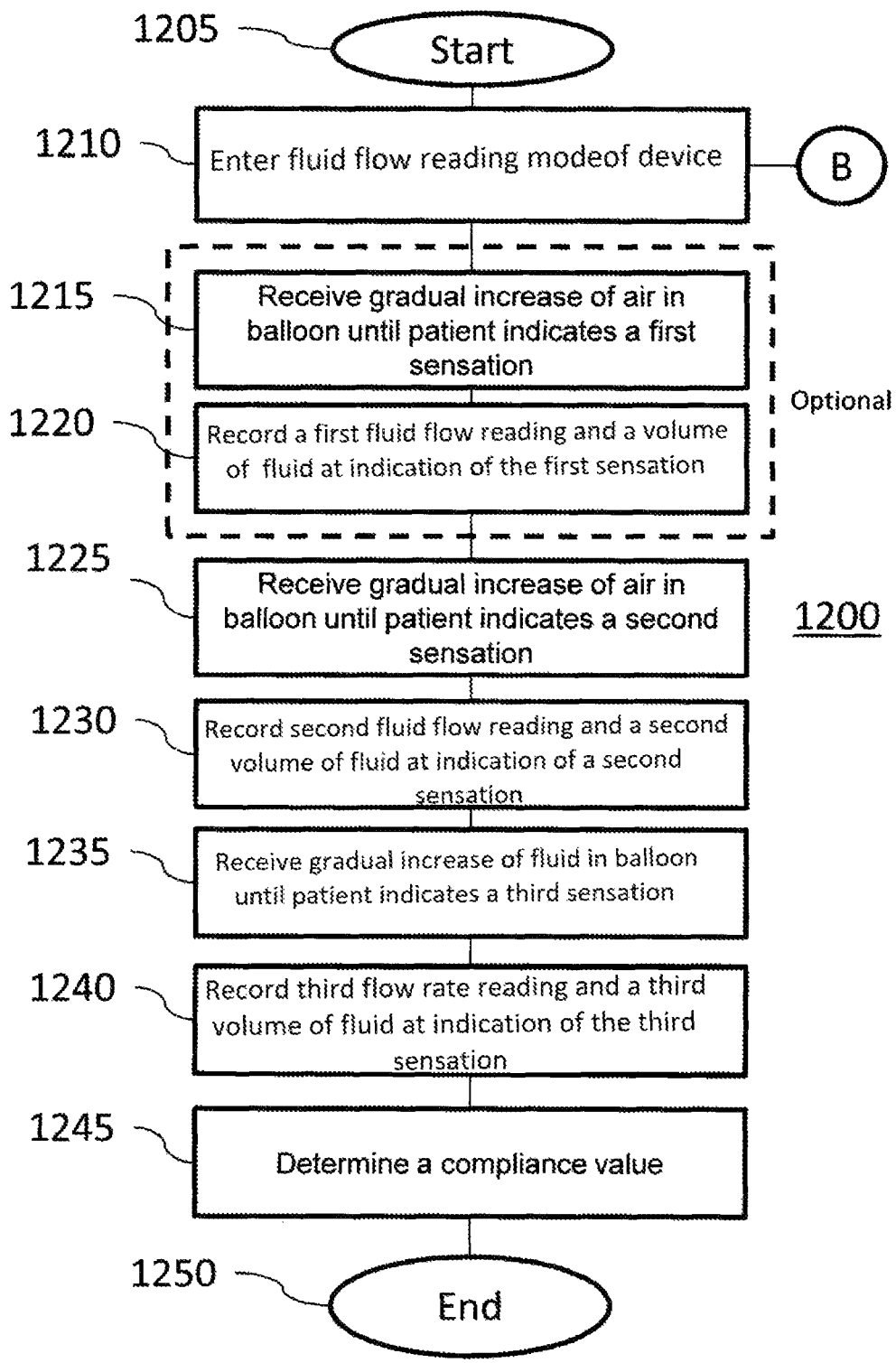
FIG. 12 is a flow chart of a method for providing rectal anal inhibitory reflex diagnostics, according to one embodiment.

FIG. 12 illustrates a diagram of a further method 1200 according to an exemplary embodiment of the invention. Method 1200 comprises a Rectal Sensation Threshold Tone and Compliance diagnostic test performed by device 700, 900. Method 1200 either starts at step 1205 or is initiated after a user proceeds from step 1115 to step 1210. At step 1210, a flow rate reading mode of the device is entered. The balloon 735 is placed in the rectal ampulla of a patient, e.g., where the marker of the secondary tube 750 is at 6 cm interior of the anal verge. The patient will be instructed to respond to at least two sensory thresholds. At step 1215, a gradual increase of fluid is received in the balloon 735 until the patient indicates a first sensation—the point at which a patient starts to feel the balloon 735 filling with fluid. With the indication of the first sensation, at step 1220, a first flow rate reading and a first volume of fluid are recorded. At step 1225, a further gradual increase of fluid is received in the balloon 735 until the patient indicates a second sensation—the point at which the patient feels the need to defecate. With the indication of the second sensation, at step 1230, a second flow rate reading and a second volume of fluid are recorded. At step 1235, a further gradual increase of fluid is received in the balloon 735 until the patient indicates a third sensation—the point at which the patient is at a maximum tolerable sensation to defecate (i.e., the patient feels that they can no longer hold in their feces). At the indication of the third sensation, at step 1240, a third flow rate reading and a third volume of fluid are recorded. At step 1245, a compliance value is determined based upon the flow rate readings and converted to appropriate units using a calibration table. These flow rate readings are recorded on the handheld device 700, 900 so that the medical professional may make notes in the patient's chart. Typical ranges for first, second, and third sensation recorded fluid volumes are 40 cc to 90 cc, 120 cc to 140 cc, and 200 cc to 300 cc, respectively. Prior art devices only record up to 300 cc maximum fluid volume. However, the present device 700, 900 may allow for recording of fluid flow rate values at volumes greater than 300 cc. The compliance value may be computed according to a difference of volumes divided by a difference of the two corresponding flow rate readings, e.g., (V3−V2)/(P3−P2). The compliance value may also be computed by a recorded volume by its corresponding flow rate reading, e.g. V2/P2. In one embodiment, the first sensation portion of the test is optional. In this embodiment, the medical professional performing the test would increase the amount of fluid in the balloon 735 until the patient feels the need to defecate.

Figure 13:
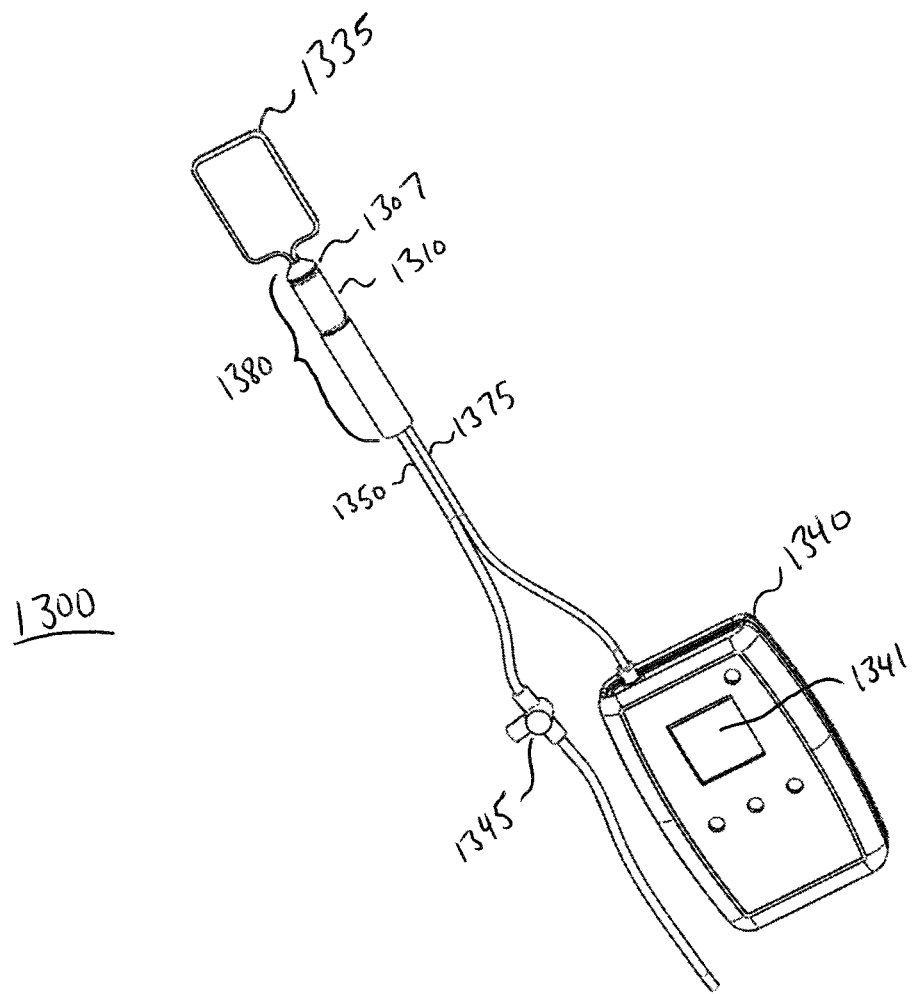
FIG. 13 is a fragmentary, perspective view of an exemplary embodiment of an analyzer according to the invention.

FIG. 13 illustrates a perspective view of an analyzer 1300 according to one exemplary embodiment. In this embodiment, the analyzer is set up to perform an anal manometry diagnostic procedure, e.g., the procedure described in method 1000. Analyzer 1300 comprises a balloon 1335, a probe 1380, a sensor 1310, a main fluid tube 1350, an electrical connection 1375, a fluid flow rate reading device 1340, and a valve 1345. The main fluid tube 1350 is disposed within the probe 1380 and is slideably engageable within the probe 1380. In this embodiment, the balloon 1335 is retracted to a distal end 1307 of the probe 1380 in order to perform an anal manometry diagnostic procedure, however for anal manometry it does not matter where the balloon is placed. To begin the anal manometry diagnostic procedure, a patient is placed in a left lateral position. Spine alignment is not needed when using the analyzer 1300. The analyzer 1300 is lubricated and inserted into the rectum. The analyzer fluid flow rate reading device 1340 communicates with the sensor 1310 via the electrical connection 1375. While looking at the analyzer fluid flow rate reading device display screen 1341, a diagnostician using the device 1300 slowly moves the analyzer back and forth in the patient's rectum to find and record both the resting and highest fluid flow rate. A fluid flow rate reading mode of device 1340 is entered. Fluid flow rate readings may be read from display screen 1341, for example, with a number indicating psi or inches of mercury. The patient rests quietly with no squeezing or straining for 20-30 seconds while a resting fluid flow rate is recorded. The resting fluid flow rate approximates the internal anal sphincter muscle. The patient is instructed to squeeze as hard as possible for 5 seconds. The maximum squeeze fluid flow rate is then recorded by the device 1340. Maximum squeeze fluid flow rate approximates the external anal sphincter muscle.

Figure 14:
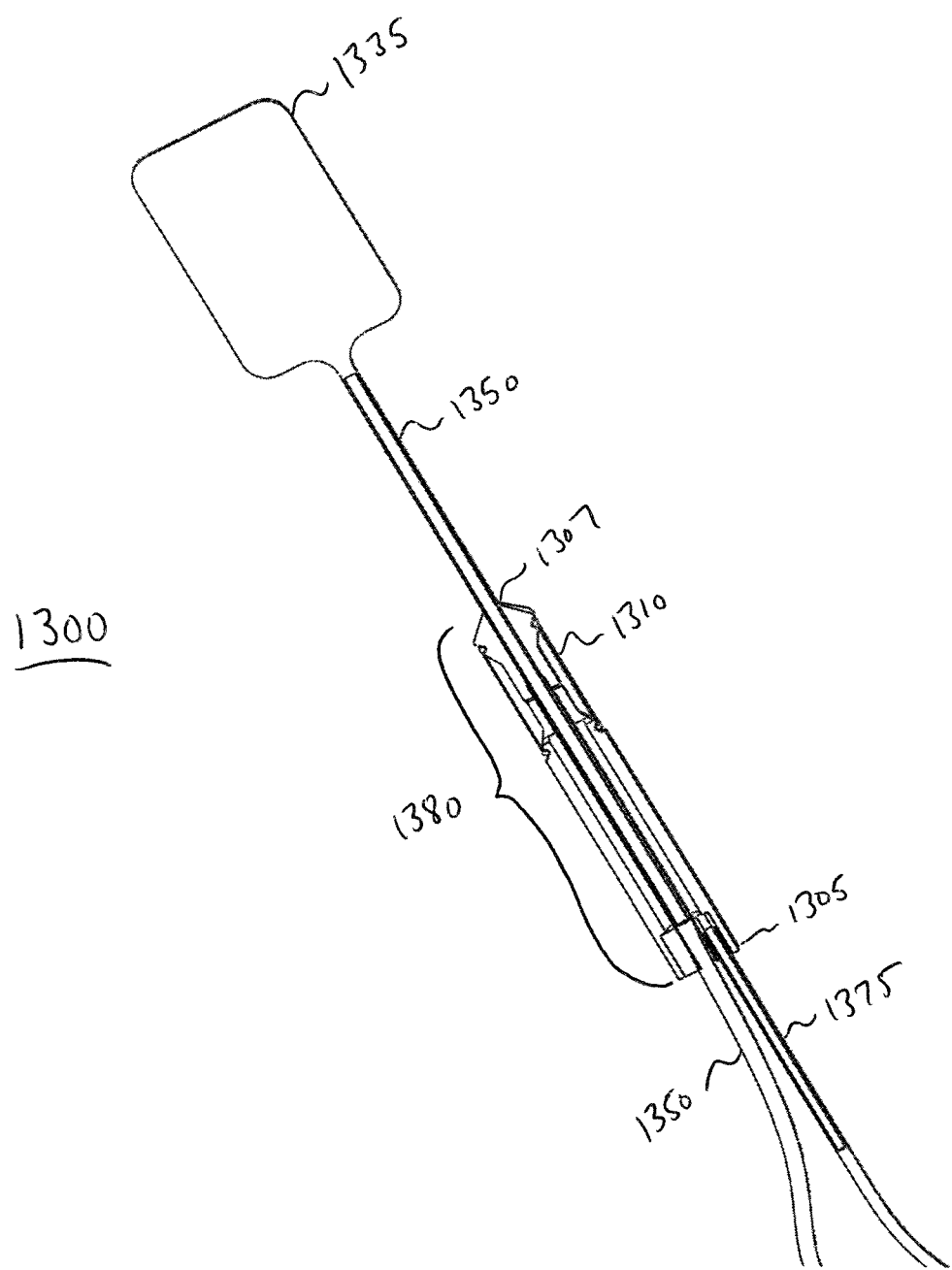
FIG. 14 is a fragmentary, enlarged, cross-sectional view of the analyzer of FIG. 13.
Figure 15:
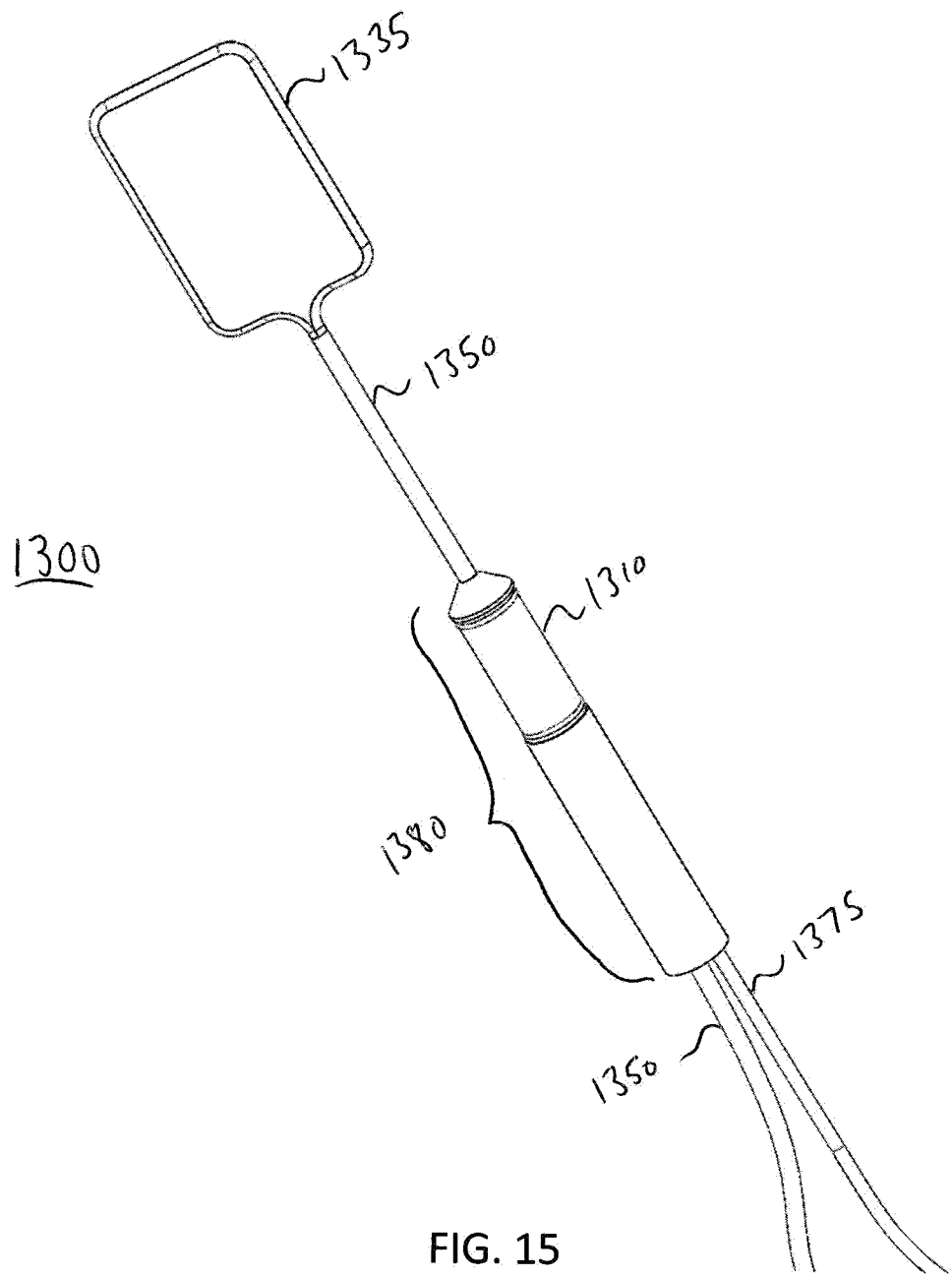
FIG. 15 is a fragmentary, perspective view of the analyzer of FIG. 13 when ready to perform Rectal Sensation Threshold Tone and Compliance diagnostic tests.
Figure 16:
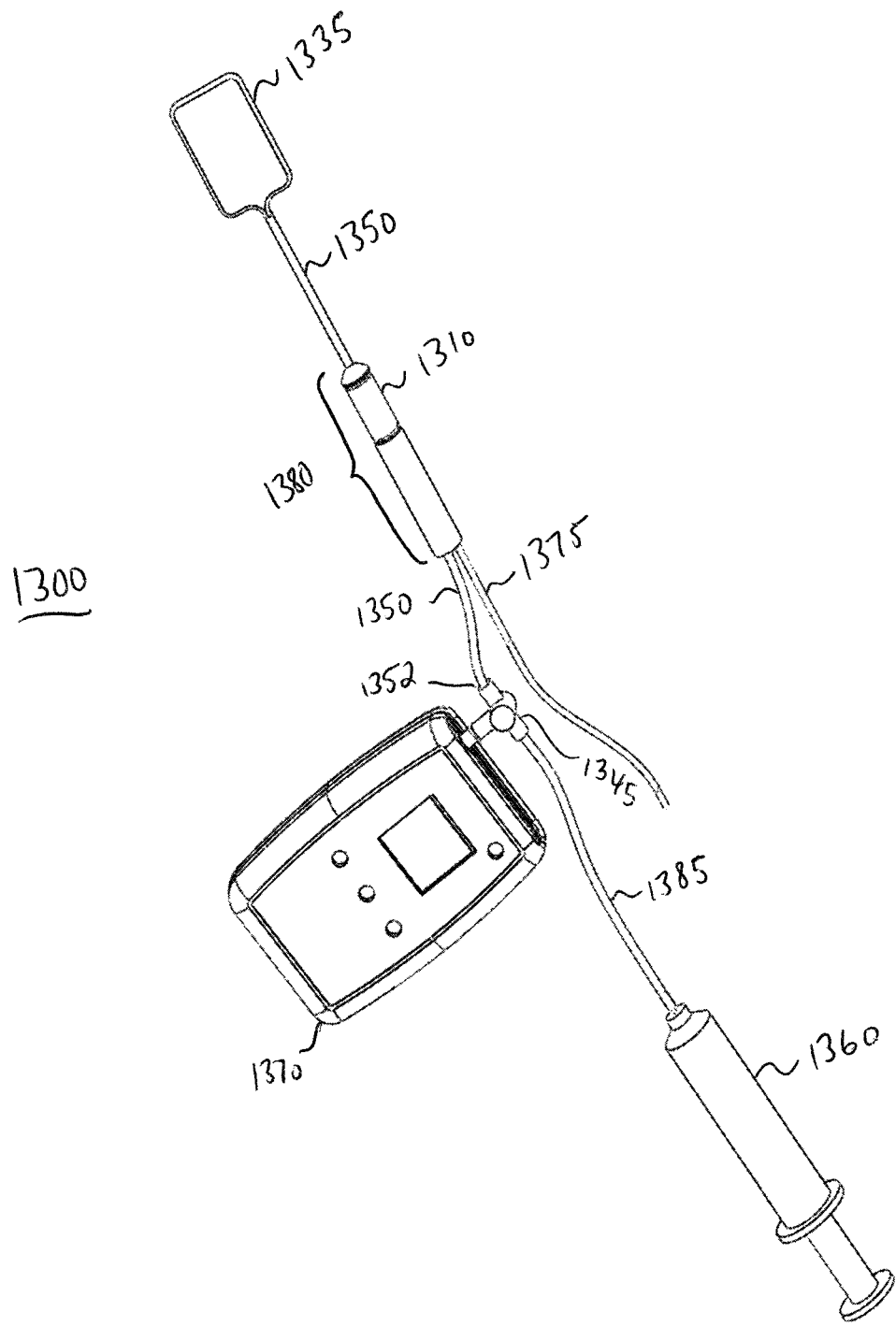
FIG. 16 is a fragmentary, perspective view of the analyzer of FIGS. 13, 14, and 15.

FIG. 14 illustrates a cross-sectional view of a distal end of the analyzer 1300. In this exemplary embodiment, the analyzer 1300 is set up to perform a Rectal Sensation Threshold Tone and Compliance diagnostic test. The analyzer 1300 comprises the balloon 1335, the probe 1380, the sensor 1310, the main fluid tube 1350, and the electrical connection or coupling 1375. In this embodiment, the balloon 1335 is extended from a distal end 1307 of probe 1380 in order to perform a Rectal Sensation Threshold Tone and Compliance diagnostic procedure, e.g., the procedure described in method 1200. The main fluid tube 1350 may be pushed through an opening in the proximal end 1305 of the probe 1380 in order to extend the balloon 1335 from the interior of the distal end 1307 of probe 1380, and further into a patient's rectum in order to perform the procedure. FIG. 15 illustrates a perspective view of the analyzer 1300 when the analyzer 1300 is set up to perform the Rectal Sensation Threshold Tone and Compliance diagnostic test. FIG. 16 illustrates a further embodiment of the elements shown in FIGS. 14 and 15. In this embodiment, FIG. 16 additionally shows a valve 1345, a fluid flow rate reading device 1370, a fluid tube 1385, and a syringe 1360. The proximal end 1352 of the fluid tube 1350 is attached to a distal side of the valve 1345 (with respect to the syringe 1360). The valve 1345 is used to prevent fluid from expelling out from balloon 1335 until desired. In one exemplary embodiment, the valve 1345 is a luer-lock, two-way valve. The valve 1345 is coupled to a fluid flow rate reading device 1370 that measures fluid flow rate on the balloon 1335.

When the balloon 1335 is extended as shown in FIGS. 14, 15, and 16, analyzer 1300 may perform a Rectal Sensation Threshold Tone and Compliance diagnostic test, e.g., method 1200. A fluid flow rate reading mode of the device 1370 is entered. The balloon 1335 is extended distally from a distal end 1307 of probe 1380 such that the balloon 1335 is placed in the rectal ampulla of a patient. The patient will be instructed to respond to at least two sensory thresholds. A gradual increase of fluid is received in the balloon 1335 until the patient indicates a first sensation—the point at which a patient starts to feel the balloon 1335 filling with fluid. With the indication of the first sensation a first fluid flow rate reading and a first volume of fluid are recorded. A further gradual increase of fluid is received in the balloon 1335 until the patient indicates a second sensation—the point at which the patient feels the need to defecate. With the indication of the second sensation, a second fluid flow rate reading and a second volume of fluid are recorded. A further gradual increase of fluid is received in the balloon 1335 until the patient indicates a third sensation—the point at which the patient is at a maximum tolerable sensation to defecate (i.e., the patient feels that they can no longer hold in their feces). At the indication of the third sensation, a third fluid flow rate reading and a third volume of fluid are recorded. A compliance value is determined based upon the fluid flow rate readings. These fluid flow rate readings are recorded on the hand-held device 1370 so that the medical professional may make notes in the patient's chart. Typical ranges for first, second, and third sensation recorded fluid volumes are 40 cc to 90 cc, 120 cc to 140 cc, and 200 cc to 300 cc, respectively. Prior art devices only record up to 300 cc maximum fluid volume. However, the device of the present invention may allow for recording of fluid flow rate values at volumes greater than 300 cc. The compliance value may be computed according to a difference of volumes divided by a difference of the two corresponding fluid flow rate readings, e.g., (V3−V2)/(P3−P2). The compliance value may also be computed by a recorded volume through its corresponding fluid flow rate reading, e.g., V2/P2. In one exemplary embodiment, the first sensation portion of the test is optional. In this embodiment, the medical professional performing the test would increase the amount of fluid in the balloon 1335 until the patient feels the need to defecate.

Figure 17:
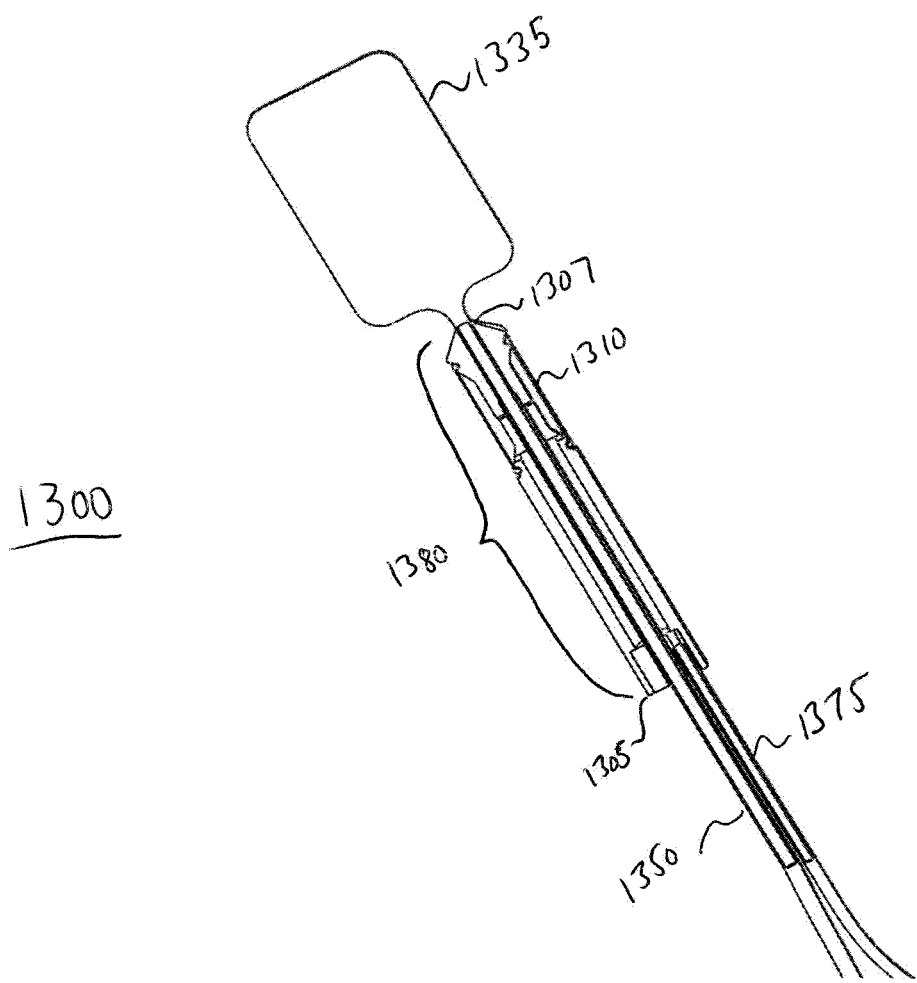
FIG. 17 is a fragmentary, cross-sectional view of the analyzer of FIG. 13.
Figure 18:
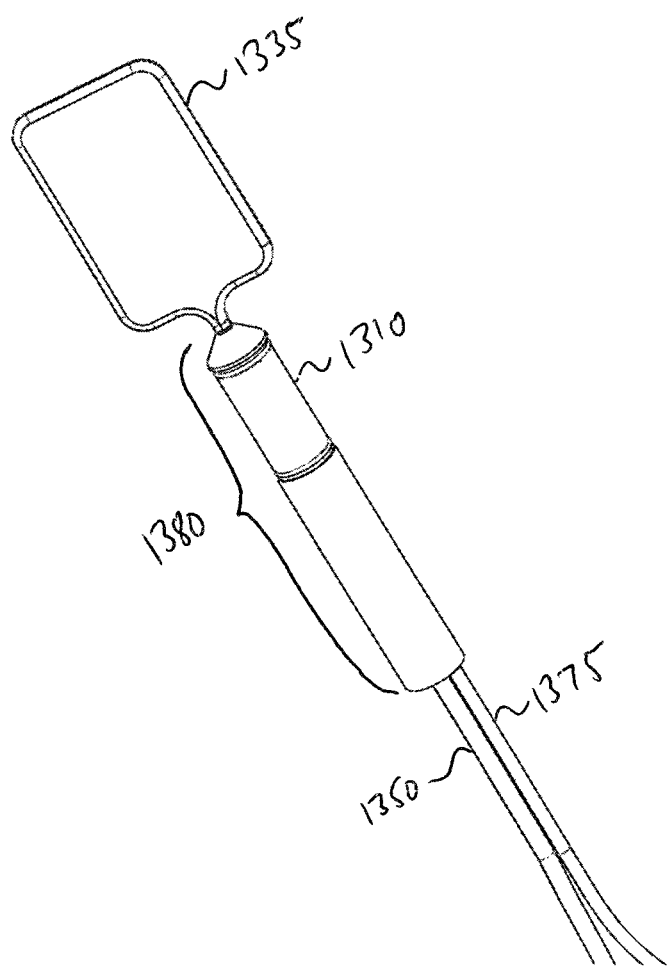
FIG. 18 is a fragmentary, perspective view of the analyzer of FIG. 13 when ready to perform a RAIR diagnostic test.
Figure 19:
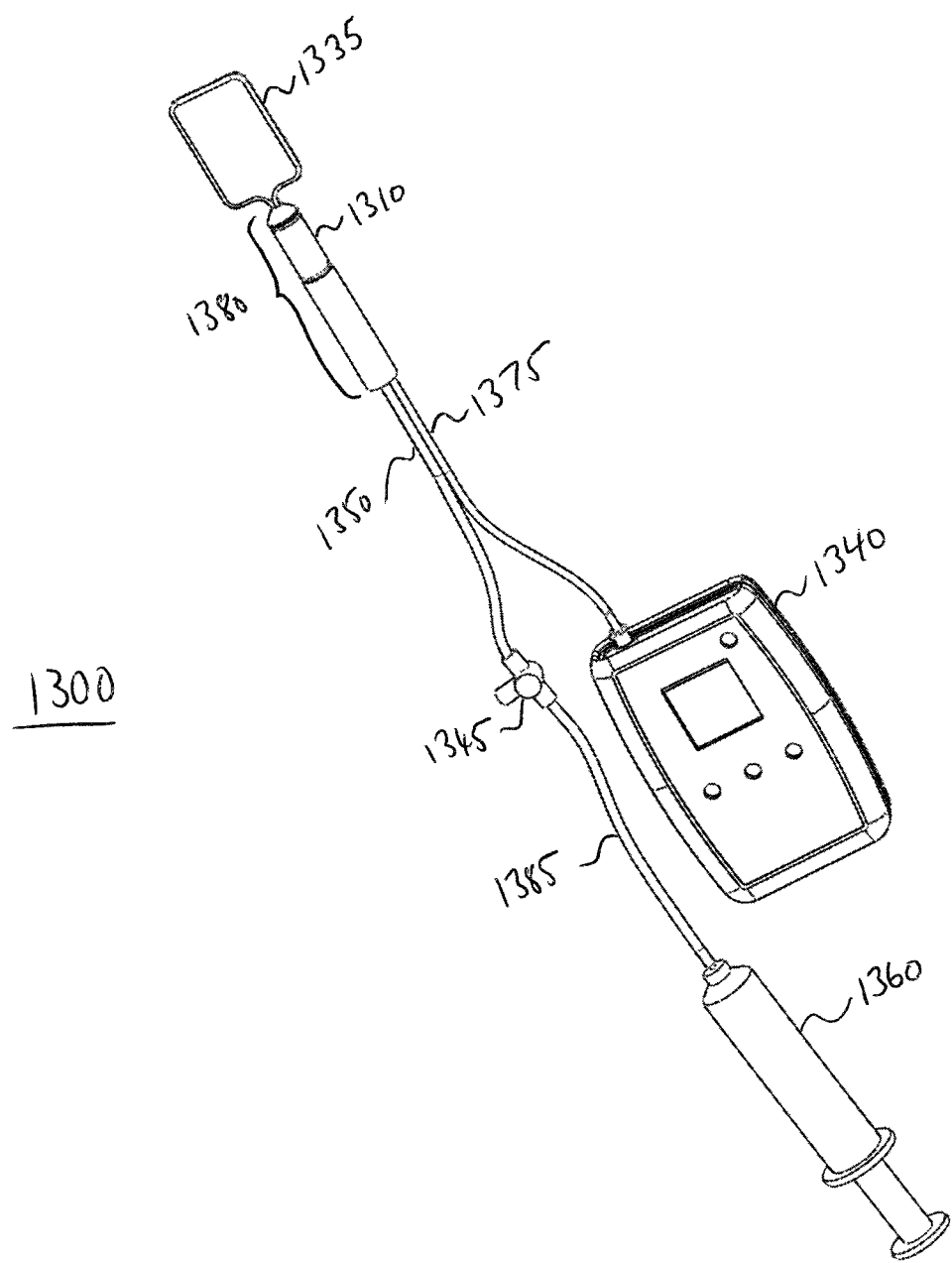
FIG. 19 is a perspective view of the analyzer of FIGS. 13, 17, and 18.

FIG. 17 illustrates a cross-sectional view of the analyzer 1300. In this exemplary embodiment, the analyzer is set up to perform a Recto-Anal Inhibitory Reflex (RAIR) diagnostic test. Analyzer 1300 comprises the balloon 1335, the probe 1380, the sensor 1310, the main fluid tube 1350, and an electrical connection 1375. In this embodiment, the balloon 1335 is retracted to a distal end 1307 of probe 1380 in order to perform a RAIR diagnostic procedure, e.g. the procedure described in method 1100. Fluid tube 1350 may be pulled through an opening in the proximal end 1305 of probe 1380 in order to retract balloon 1335 to the distal end 1307 of probe 1380 in order to perform the procedure. FIG. 18 illustrates a perspective view of analyzer 1300 when the analyzer is set up to perform the RAIR diagnostic test. FIG. 19 illustrates a further embodiment of the elements shown in FIGS. 17 and 18. In this embodiment, FIG. 19 additionally shows a valve 1345, a fluid flow rate reading device 1340, a fluid tube 1385, and a syringe 1360. The proximal end 1352 of the fluid tube 1350 is attached to the distal side of the valve 1345. The valve 1345 is used to prevent fluid from expelling out from balloon 1335 until desired. In one exemplary embodiment, the valve 1345 is a luer-lock, two-way valve. The valve 1345 is coupled to a fluid flow rate reading device 1340 that measures fluid flow rate from the sensor 1310.

Figure 24:
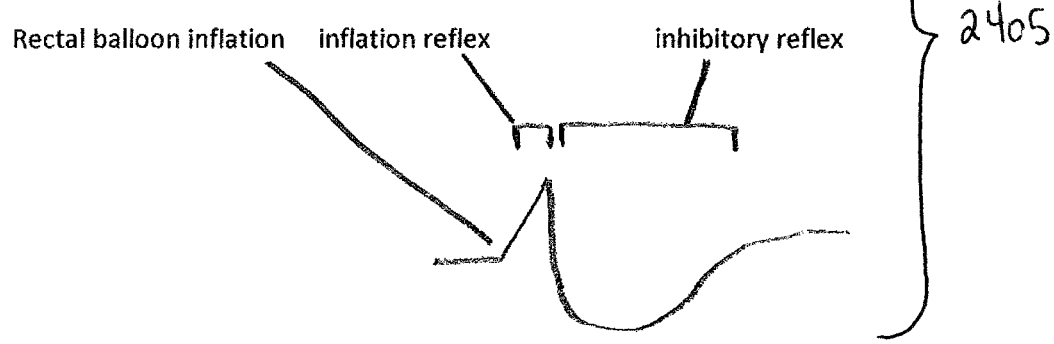
FIG. 24 is a diagrammatic illustration of a display shown on the analyzer according to the invention during a RAIR test with both normal and abnormal plots.
Figure 24:
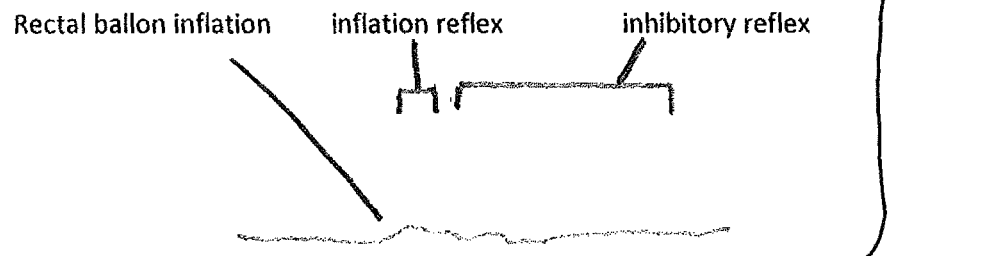

The analyzer 1300 may perform a Recto-Anal Inhibitory Reflex (RAIR) diagnostic test, e.g., in accordance with method 1100. A graphing mode of the device 1340 is entered. The analyzer 1300 should be within the rectum at the high resting fluid flow rate zone of the patient. A patient response to rapid introduction of fluid into and rapid withdrawal of fluid out from the balloon 1335 is measured. The balloon is inserted further into the rectum and, using an inflation device, e.g., syringe 1360, 40 cc to 60 cc of fluid is abruptly plunged into balloon 1335. Within 2 to 4 seconds thereafter, the fluid is completely withdrawn from the balloon. The fluid flow rate reading on the display 1341 can be used to identify whether RAIR is present. Exemplary graphs 2405, 2410 in FIG. 24 showing possible visual responses for a RAIR diagnostic test on a graph meter, e.g., a graph mode presented on display 1341, for both normal and abnormal conditions. Recto-anal inhibitory reflex describes the relaxation of the internal anal sphincter in response to distention of the rectum. Graph 2405 shows a visual representation of what a graph meter would record if RAIR is present, i.e., a normal condition. Graph 2410 shows a visual representation of what a graph meter would record if RAIR is not present, i.e., an abnormal condition. When the balloon 1335 is rapidly inflated, a normal patient will exhibit a particular reflex shown, for example, in graph 2405. Absence of such a reflex (see graph 2410) is a clear indication of Hirschsprung's disease.

Figure 20:
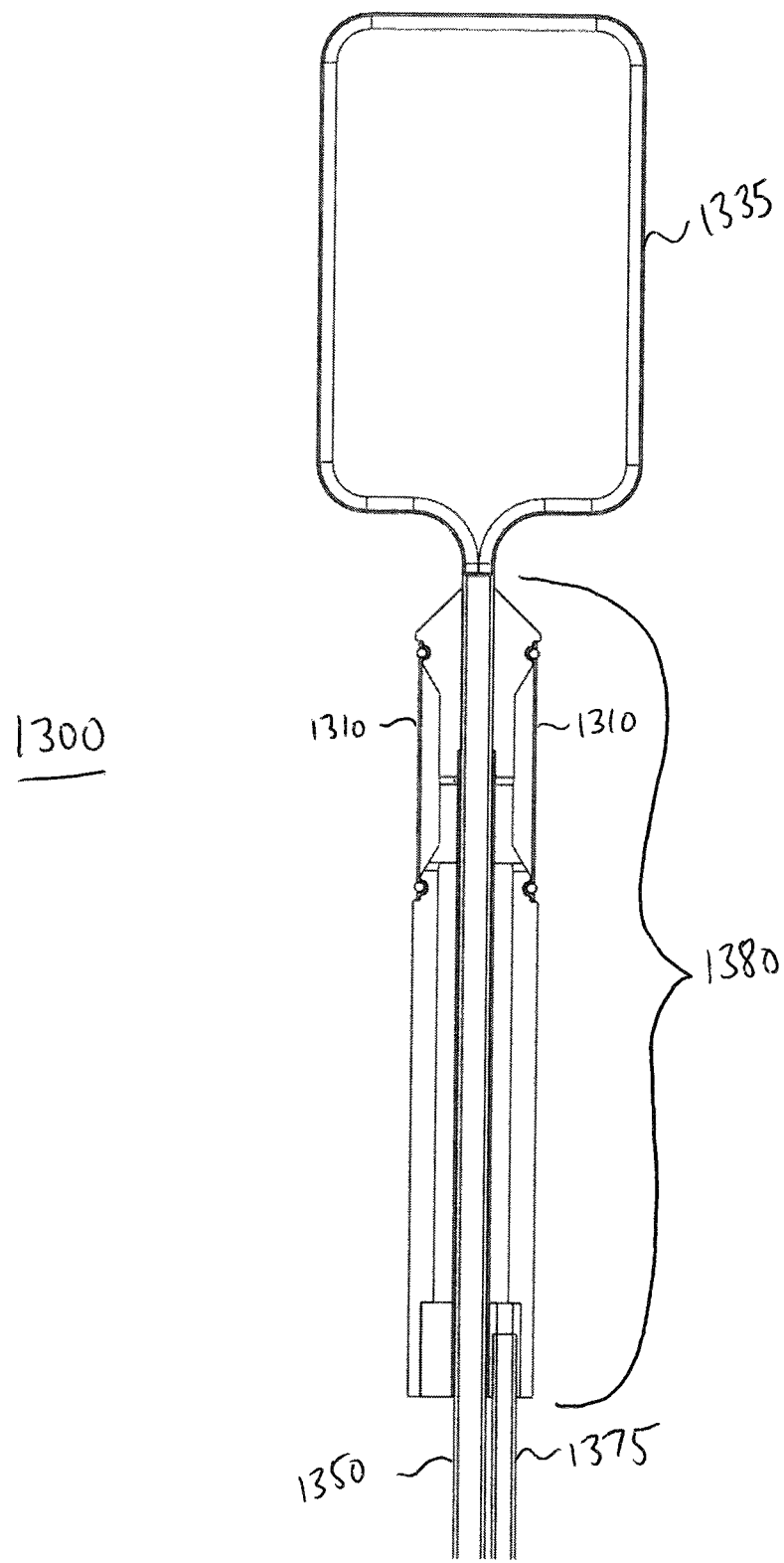
FIG. 20 is a fragmentary, cross-sectional plan view of the analyzer of FIG. 13.

FIG. 20 illustrates a cross-sectional view of the analyzer 1300. In this exemplary embodiment, the analyzer 1300 is set up to perform either an anal manometry diagnostic test or a Recto-Anal Inhibitory Reflex (RAIR) diagnostic test. The analyzer 1300 comprises the balloon 1335, the probe 1380, the sensor 1310, the main fluid tube 1350, and the electrical connection 1375. In this embodiment, the balloon 1335 is extended from a distal end 1307 of probe 1380 in order to perform, e.g., methods 1000 and 1100. The fluid tube 1350 may be pulled through an opening in the proximal end 1305 of probe 1380 in order to retract balloon 1335 to the distal end 1307 of probe 1380 in order to perform any of the diagnostic procedures as desired.

Figure 21:
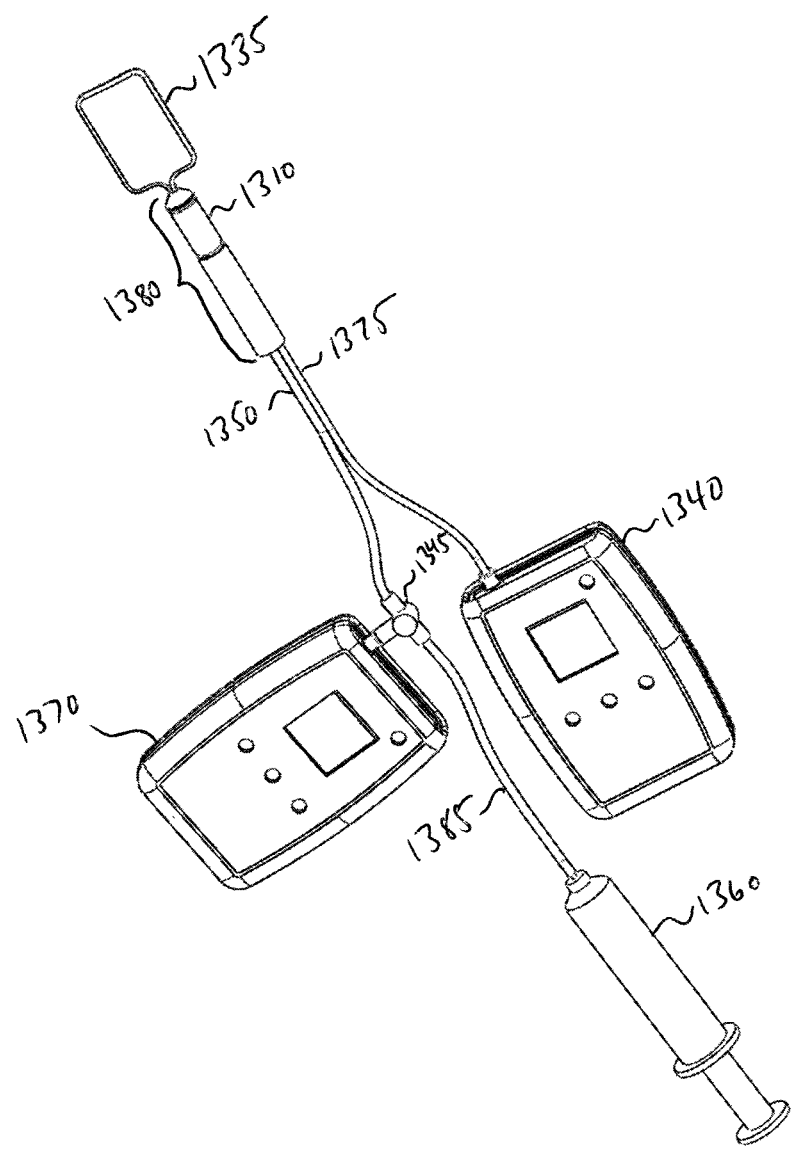
FIG. 21 is a perspective view of another exemplary embodiment of the analyzer of FIG. 13.

FIG. 21 illustrates a perspective view of the analyzer 1300, which comprises the balloon 1335, the probe 1380, the sensor 1310, the main fluid tube 1350, and the electrical connection 1375. In this exemplary embodiment, the balloon 1335 is extended from a distal end 1307 of the probe 1380 in order to perform, e.g., methods 1000 and 1100. The fluid tube 1350 may be pulled through an opening in the proximal end 1305 of probe 1380 in order to retract balloon 1335 to the distal end 1307 of probe 1380 and perform any of the diagnostic procedures mentioned. In this embodiment, additionally shown is a valve 1345, a fluid flow rate reading device 1370, a fluid tube 1385, and syringe 1360. The proximal end 1352 of fluid tube 1350 is attached to the distal side of the valve 1345. The valve 1345 is used to prevent fluid from expelling out from balloon 1335 until desired. In one exemplary embodiment, the valve 1345 is a luer-lock, two-way valve. The valve 1345 is coupled to a fluid flow rate reading device 1370 that measures fluid flow rate on the balloon 1335. The valve 1345 is also coupled to a fluid flow rate reading device 1340 that measures fluid flow rate from sensor 1310. Although fluid flow rate reading devices 1340, 1370 are shown as separate devices, the functionality for each of these devices may be combined into one fluid flow rate reading device that measures fluid flow rates from sensor 1310 and fluid flow rates exerted on balloon 1335.

Figure 22:
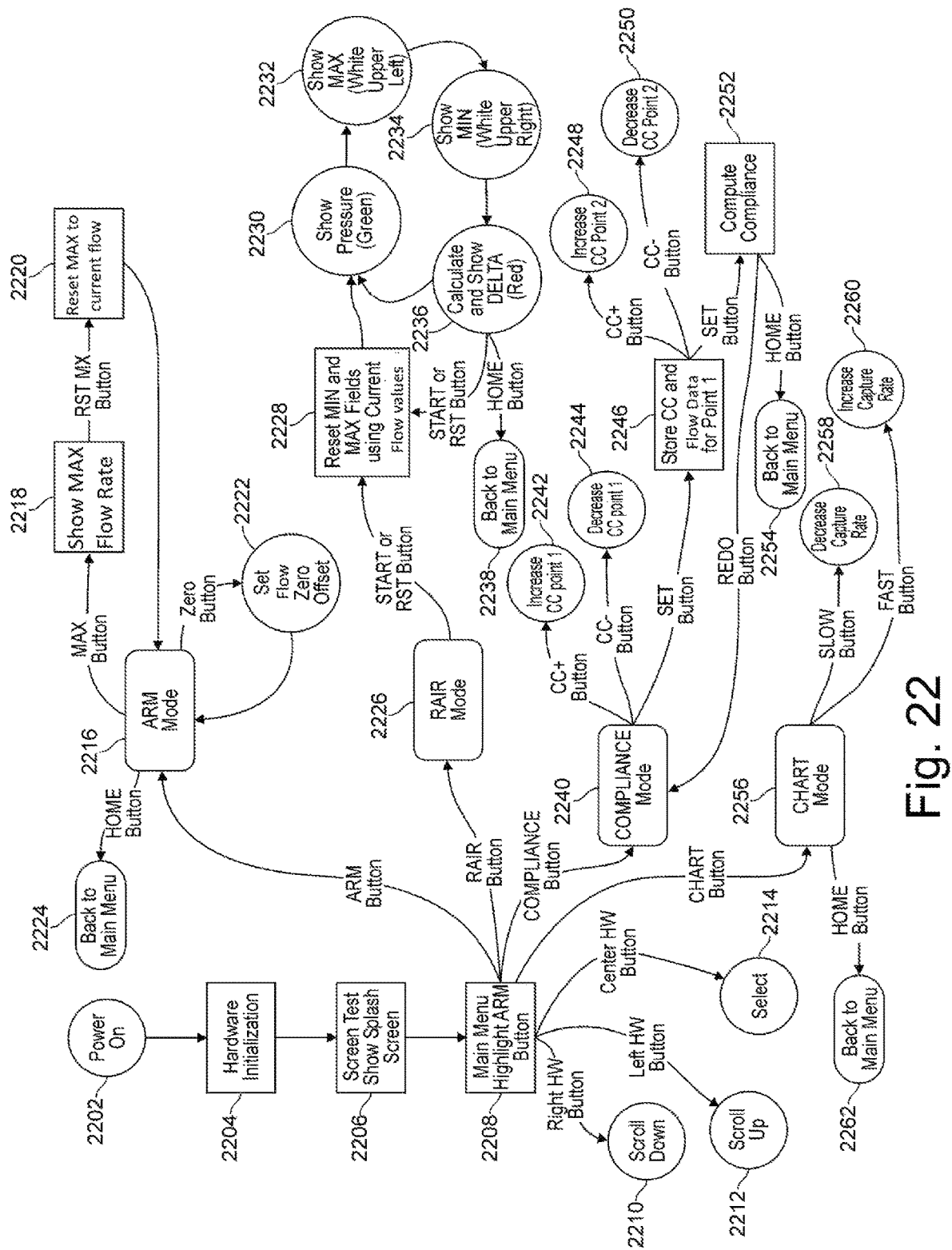
FIG. 22 is a user interface flow diagram for an exemplary embodiment for operating the analyzer according to the invention.

FIG. 22 illustrates a user interface flow diagram for the analyzer 700, 900, 1300 according to one exemplary embodiment of the invention. The analyzer is powered on at step 2202. At step 2204, hardware initialization is performed. At step 2206, a screen test is performed and, for example, a splash screen is shown. At step 2208, the main menu is shown. In one exemplary embodiment, an Ano-Rectal Manometry (ARM) button is highlighted initially. Although the present embodiments show a device having a device that uses a screen in conjunction with hardware buttons, the present disclosure also contemplates use of a touch screen and soft keys or any other equivalent user interfaces, including voice commands. A user of the device 700, 900, 1300 may use one hardware button to scroll down 2210 (e.g., a right button), another hardware button to scroll up 2212 (e.g., a left button), and a third hardware button 2214 (e.g., a center button) to select a diagnostic test.

When the ARM mode option is selected, ARM mode is entered at 2216. A current maximum fluid flow rate is shown 2218 when a MAX button is selected. The MAX may be reset to a current fluid flow rate 2220 by pressing a RST MX button. A zero offset of a fluid flow rate may be set at 2222 by pressing a ZERO button. A user may return to the main menu 2224 by pressing a HOME button.

When the RAIR mode option is selected, RAIR mode is entered at 2226. At step 2228, MIN and MAX fields may be reset using current fluid flow rate values when a user presses the START or RST button. A fluid flow rate is shown 2230 and may be illustrated as green, for example. A MAX fluid flow rate is shown 2232 and may be illustrated in white in an upper left section of the device screen, for example. A MIN fluid flow rate is shown 2234 and may be illustrated in white in an upper right section of the device screen, for example. A difference (DELTA) between MAX 2232 and MIN 2234 is calculated at 2236 and shown on the device screen. DELTA is signified, for example, by the color red. A user may redo the diagnostic test by pressing the START or RST button. The user may return to the Main Menu 2238 by pressing the HOME button.

When a COMPLIANCE button is selected, the COMPLIANCE mode is entered at 2240. At least two data points are captured during a COMPLIANCE test. In one embodiment, three data points may be captured. A CC+ button may be used to increase fluid volume in the balloon, e.g., balloon 735, 1335, to obtain a first data point 2242. A CC− button is used in order to decrease fluid volume in the balloon for the first data point 2244. At step 2246, volume (CC) and fluid flow rate data are stored for the first data point. A CC+ button is used in order to increase fluid volume in the balloon for a second data point 2248. A CC− button is used in order to decrease fluid volume in the balloon for the second data point 2250. At step 2252, a compliance value is computed when a user selects the SET button. A user may redo the diagnostic test by pressing the REDO button and may return to the Main Menu 2254 by pressing the HOME button.

When a CHART button is selected, a CHART mode is entered at 2256. A capture rate is decreased at step 2258 by pressing the SLOW button. A capture rate is increased at step 2260 by pressing a FAST button. A user may return to the Main Menu 2262 by pressing the HOME button.

Figure 23:
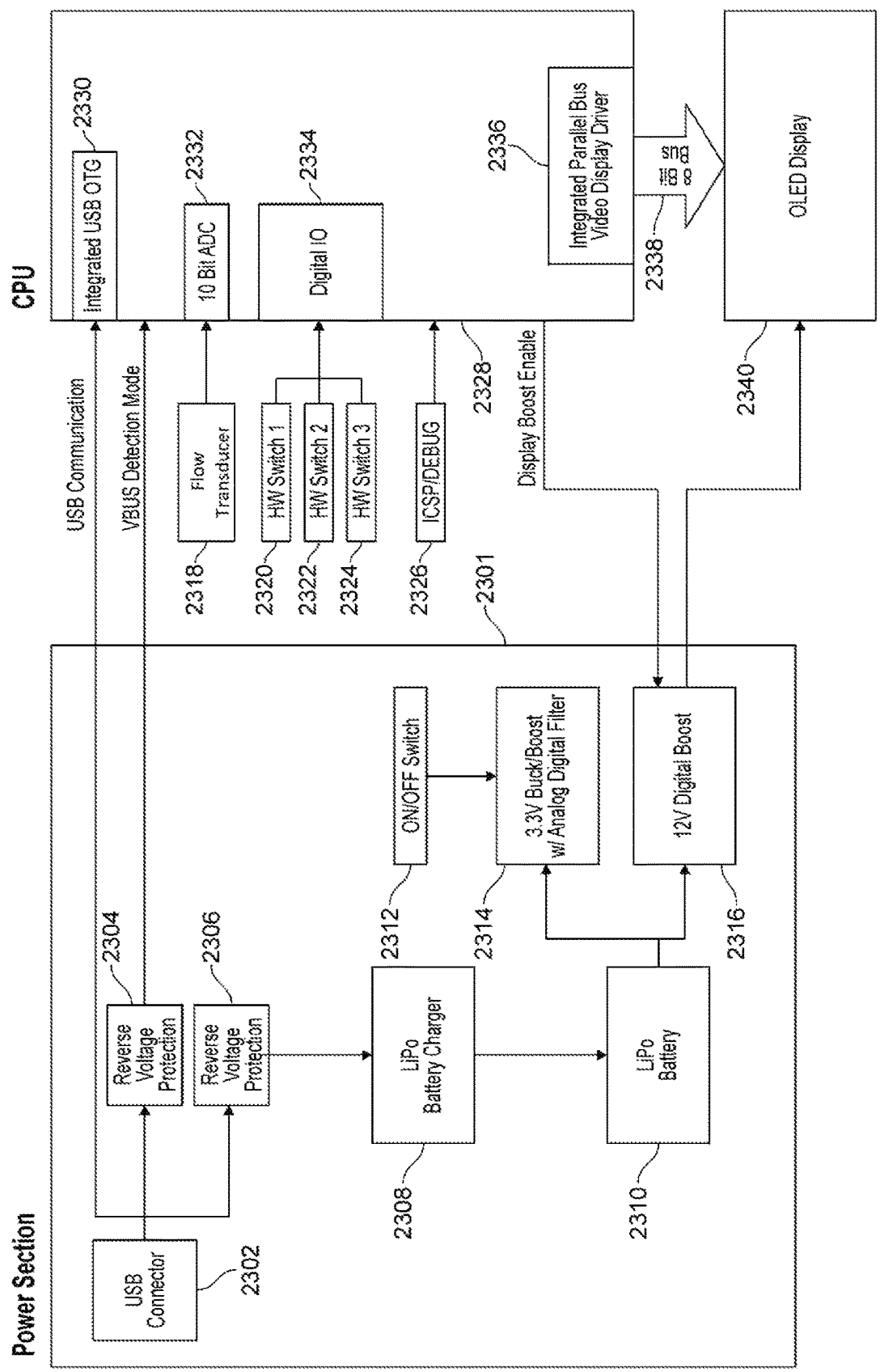
FIG. 23 is a block circuit diagram of an exemplary embodiment of an electronics architecture according to the invention.

FIG. 23 illustrates an electronics architecture 2300 according to one exemplary embodiment of the invention. Electronics architecture 2300 comprises a power section 2301, a central processing unit (CPU) section 2328, and a display 2340. Power section 2301 has a universal serial bus (USB) connector 2302 that is coupled to communicate with a CPU 2328 through an integrated USB on-thego (OTG) interface 2330. The USB connector 2302 communicates virtual bus (VBUS) Detection Mode information to CPU 2328 through reverse voltage protection 2304. In addition, the USB connector 2302 provides power to the battery charger 2308 through the reverse voltage protection 2306. Battery charger 2308 charges the battery 2310. In one exemplary embodiment, the battery charger 2308 is a Lithium Polymer (LiPo) battery charger and the battery 2310 is a LiPo battery. The battery 2310 is coupled to buck/boost power supply 2314 and a display boost 2316. In one exemplary embodiment, the buck/boost 2314 is a 3.3V Buck/Boost with an Analog/Digital filter. In one exemplary embodiment, the display boost 2316 is a 12V display boost. The power section 2301 also includes an ON/OFF switch 2312 coupled to the buck/boost 2314.

The CPU section 2328 is connected to a fluid flow rate transducer 2318 through a 10-bit analog-to digital converter 2332. The CPU 2328 is also connected with hardware switches 2320, 2322, 2324 through a digital input/output 2334. The CPU 2328 sends information to the display 2340 through an integrated parallel Bus video display driver 2336 and an 8-bit Bus 2338. In one exemplary embodiment, display 2340 is an OLED display.

FIG. 24 illustrates graphs 2405, 2410 showing possible visual responses for a RAIR diagnostic test on a graph meter, e.g. graph mode presented on display 1341, according to one embodiment. Recto-anal inhibitory reflex describes the relaxation of the internal anal sphincter in response to distention of the rectum. RAIR has been described above with respect to FIGS. 11, 17, 18, and 19. Graph 2405 shows a visual representation of what a graph meter would record if RAIR is present, i.e., a normal condition. Graph 2410 shows a visual representation of what a graph meter would record if RAIR is not present, i.e., an abnormal condition.

Figure 25:
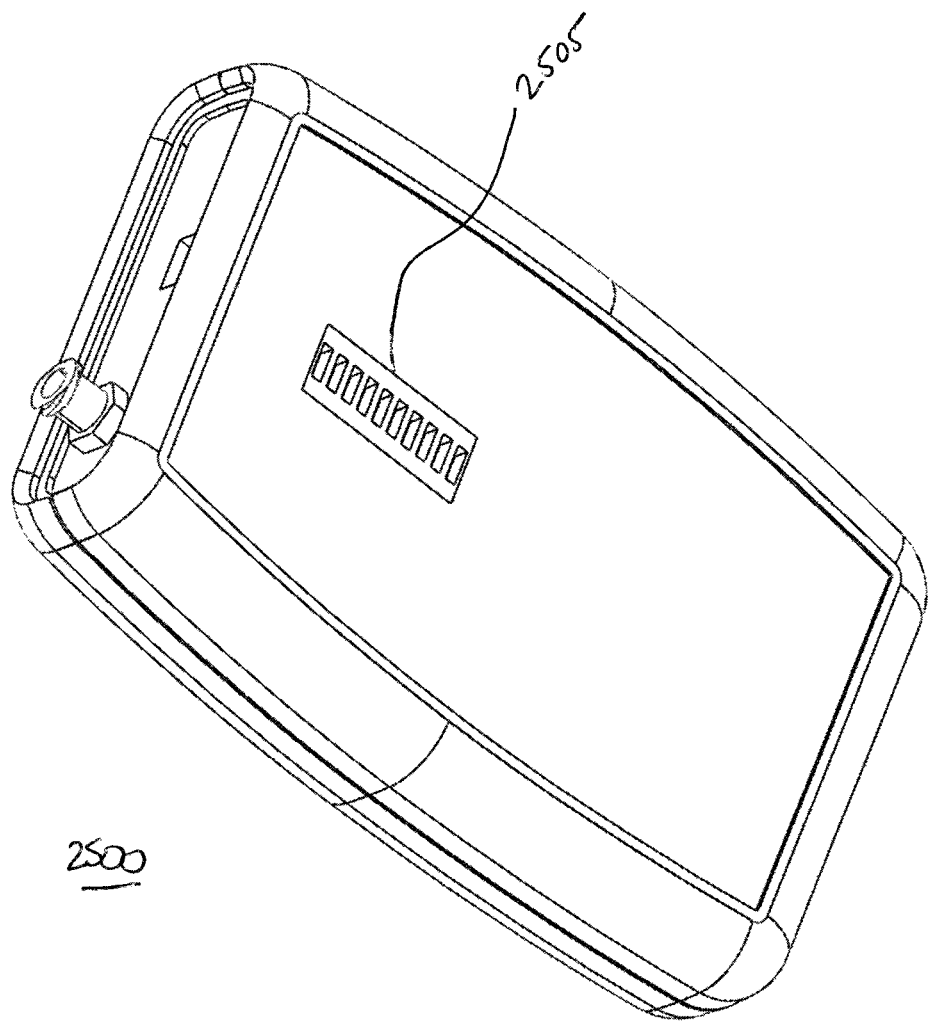
FIG. 25 is a top perspective view of a handheld device 2500 that provides biofeedback, according to one embodiment.

FIG. 25 is a top perspective view of a handheld device 2500 that provides biofeedback, according to one embodiment. The biofeedback is provided via an array of lights 2505 that illuminate in sequence as the Anorectal force increases. This device, similar to the devices depicted in FIGS. 2, 3, and 4, is intended for use by the patient at home after therapy with the physician. This device is used in conjunction with standard Anorectal probes commercially available.

Figure 26:
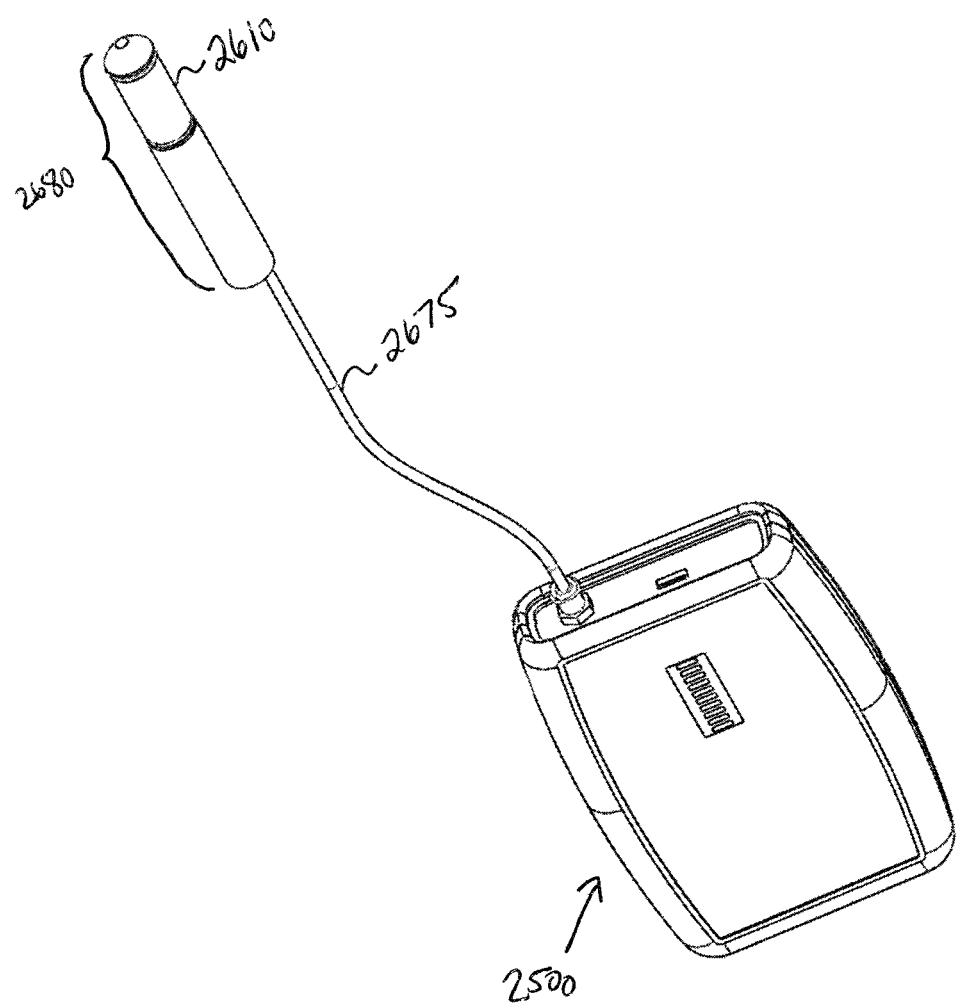
FIG. 26 is a perspective view of handheld device 2500 for use with a probe, according to one embodiment.

FIG. 26 is a perspective view of handheld device 2500 for use with a probe, according to one embodiment. Handheld device 2500 is connected to an electrical connection 2675. Electrical connection 2675 is in turn coupled to sensor 2610 of probe 2680. As stated above with respect to FIG. 25, probe 2680 may be a standard anorectal probe that is commercially available.

Figure 27:
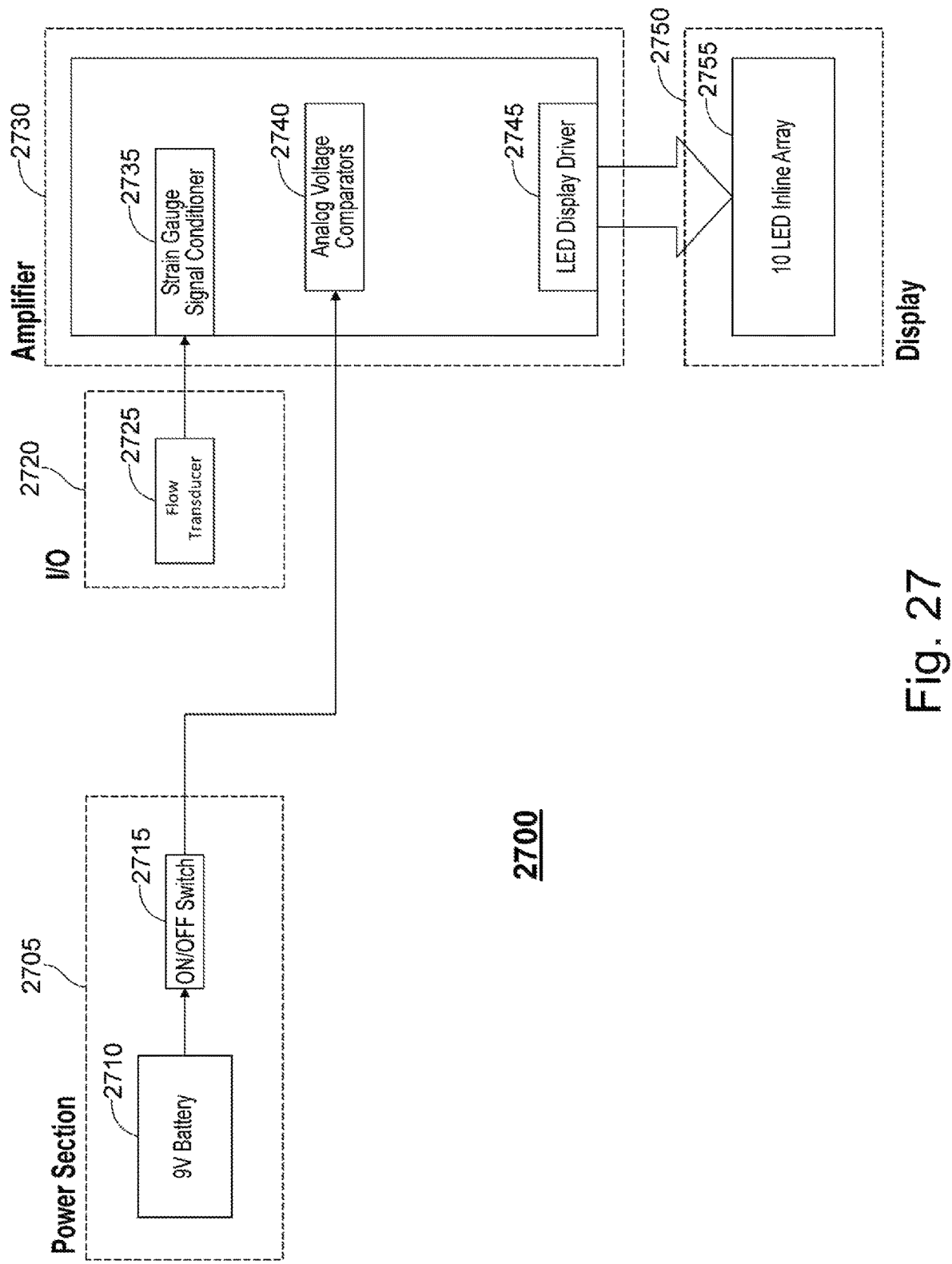
FIG. 27 is a block circuit diagram of an exemplary embodiment of an electronics architecture according to the invention.

FIG. 27 is an electronics architecture 2700 according to one embodiment. Electronics architecture 2700 may comprise the internal electronics of handheld device 2500. Electronics architecture 2700 comprises a power section 2705, and input/output section 2720, an amplifier section 2730, and a display section 2750. Power section has a battery 2710 and an ON/OFF switch 2715. Battery 2710 may be a 9V battery or any other batter capable of providing power to device 2500, 2600, 2700. Power is provided to amplifier section 2730 via ON/OFF switch 2715. Amplifier section 2730 receives a fluid flow rate indication from fluid flow rate transducer 2725 via input/output section 2720. The fluid flow rate indication is received at amplifier 2730 via the strain gauge signal conditioner 2735. Amplifier 2740 also comprises analog voltage comparators 2740 and light emitting diode (LED) display driver 2745. LED display driver 2745 to display section 2750 in order to provide biofeedback to a user of the device depicted in FIG. 26. In one embodiment, display 2750 is a 10 LED inline array 2755.

Figure 28:
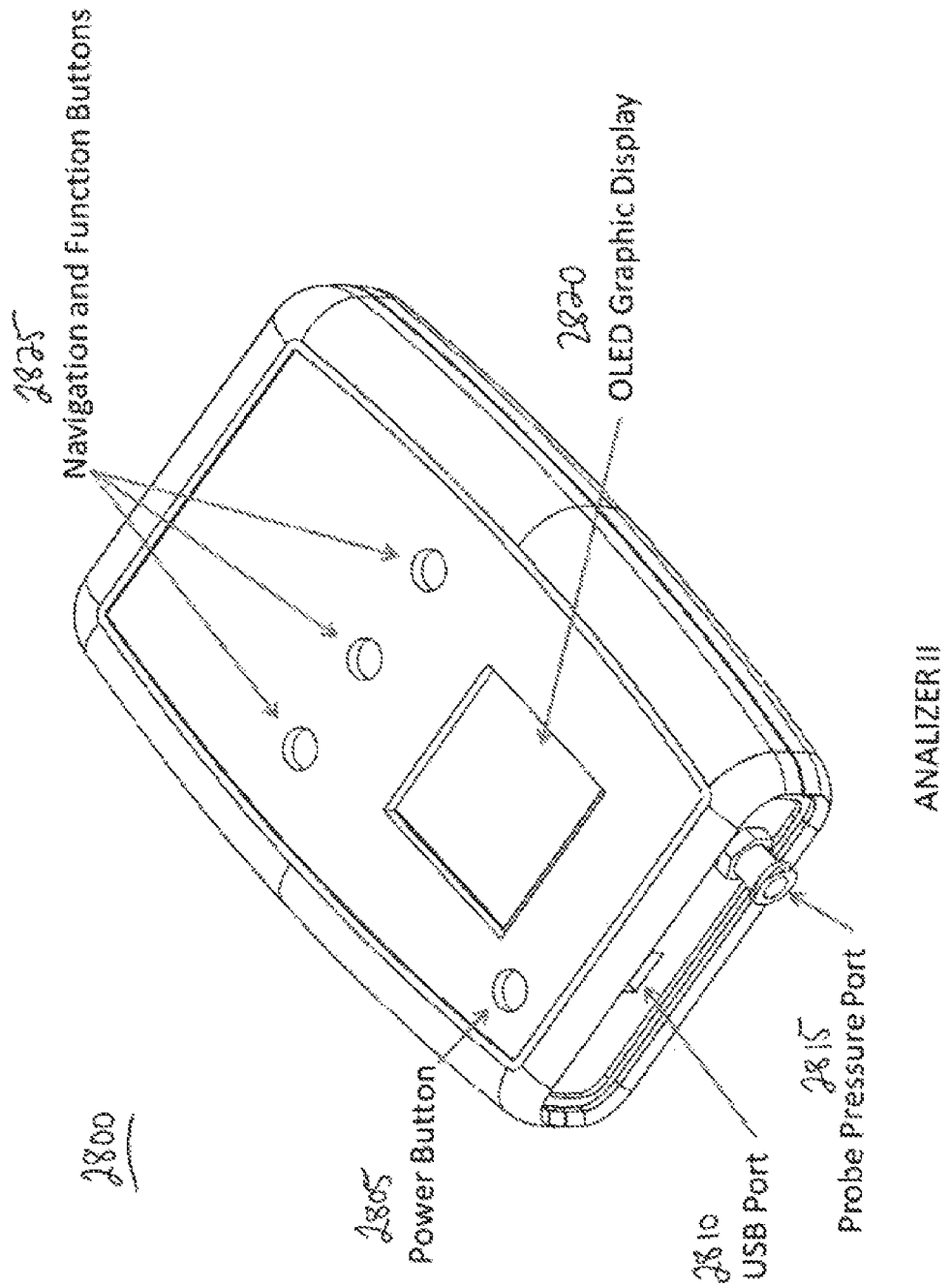
FIG. 28 is a device 2800 for providing pelvic region diagnostic information, according to one embodiment.

FIG. 28 illustrates a device 2800 for providing pelvic region diagnostic information, according to one embodiment. Device 2800 may be used in conjunction with analyzer 1300 as for example, fluid flow rate reading device 1340 and/or fluid flow rate reading device 1370. Device 2800 has a power button 2805, a USB port 2810, a probe fluid flow rate port 2815, a graphic display 2820, and navigation and function buttons 2825. In one embodiment, graphic display 2820 is an organic light emitting diode (OLED) display.

Figure 29:
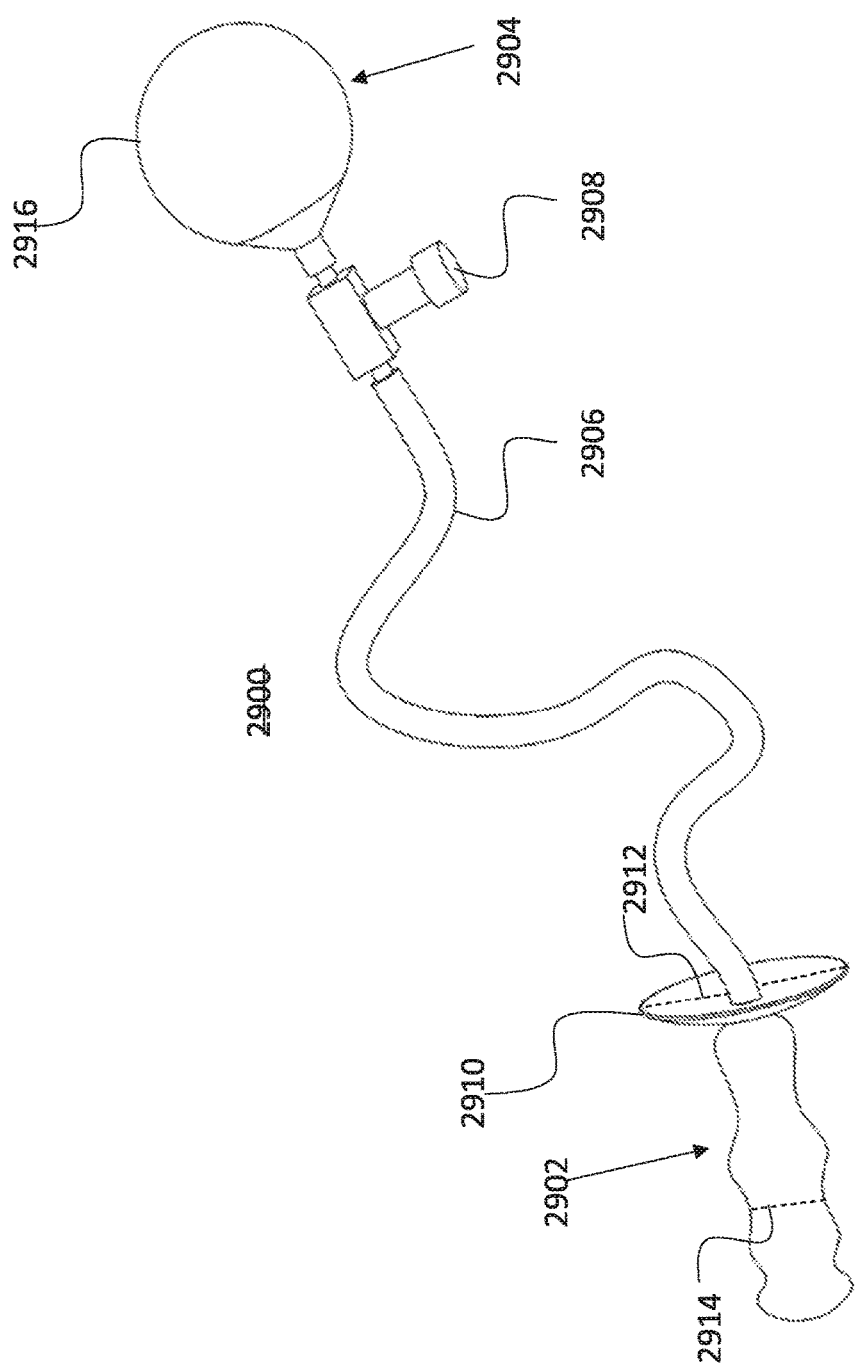
FIG. 29 is a perspective view of an exemplary embodiment of a therapeutic pelvic region analyzer according to the invention.

FIG. 29 illustrates a therapeutic pelvic region analyzer 2900 for providing pelvic region therapy. In one embodiment, the analyzer 2900 includes an expandable device 2902, a reservoir 2904, and a tube 2906 defining a fluid-flow path between the expandable device 2902 and the reservoir 2904. In use, such as when the expandable device 2902 is inserted into the pelvic region of a user, the user may be instructed to fill the expandable device 2902 by squeezing the previously filled reservoir 2904 to move an amount of fluid from the reservoir 2904 through the flow control valve 2908 to distend the expandable device 2902. The user may then be instructed to push an amount of fluid from the expandable device 2902 in a direction toward the reservoir 2904 by contracting their pelvic muscles. A fluid flow control valve 2908 provides a selectively variable level of resistance as the fluid passes from the expandable device 2902 to the reservoir 2904. Such configuration advantageously allows the user to apply stress to the pelvic muscles in response to the level of resistance to strengthen the pelvic muscles and improve the endurance of the pelvic muscles. This presents a significant advantage over existing devices used during anorectal manometry that are limited to indicating the fluid flow rate and strength of the pelvic muscles, without providing any therapeutic advantage. As a further advantage, the analyzer 2900 allows the user to exercise and retrain the pelvic muscles building strength and stamina self-sufficiently and in a private setting, e.g., the user's home. The analyzer 2900 is not limited to use in a private setting; rather, the analyzer 2900 may be used in physician's offices, hospitals, and other medical diagnostic settings.

Figure 30:
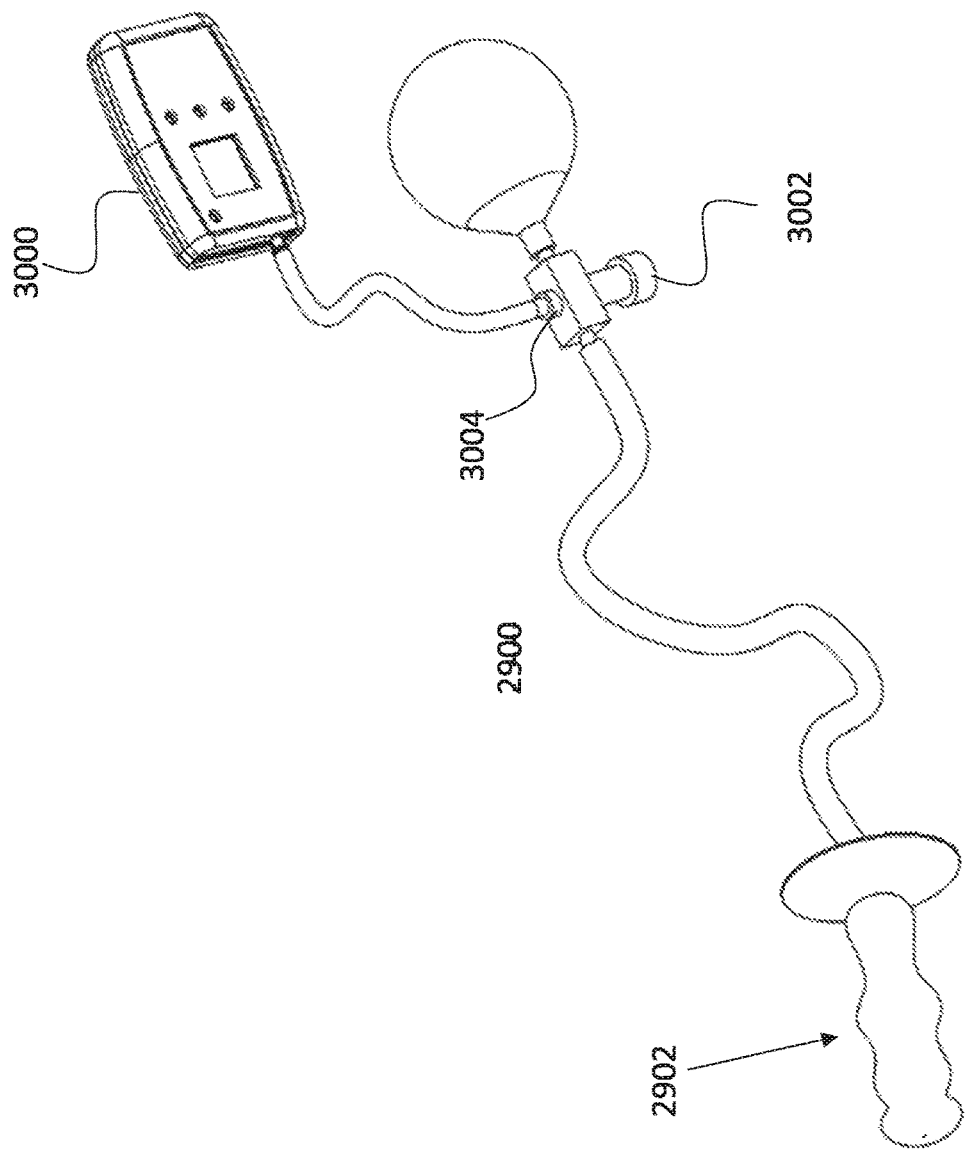
FIG. 30 is a perspective view of the therapeutic pelvic region analyzer of FIG. 29 having a flow rate and flow volume reading device coupled thereto according to the invention.

The analyzer 2900 includes the expandable device 2902 sized and shaped for insertion into an opening in a pelvic region of the user. For example, the expandable device includes a length that is at least twice as long as a width 2914 of the expandable device 2902. As described above with respect to the analyzer 200, the pelvic region can be anal or vaginal. In a preferred embodiment, the expandable device 2902 is a distention bag provided in a folded and collapsed configuration prior to insertion into the pelvic region of the user. In another embodiment, the expandable device 2902 may be a balloon, with or without the features describe above with respect to the balloon 1335 of FIGS. 13-21. In a preferred embodiment, the expandable device 2902 is made of a non-elastic material to prevent the fluid from being automatically pushed back into the reservoir 2904. The use of the nonelastic material may also result in a more precise fluid flow rate measurement reading when compared to the fluid flow rate reading obtained when elastic materials are used. Said another way, the use of the nonelastic material does not influence the fluid flow rate measurements obtained when using the analyzer 2900 coupled to a fluid flow rate reading device 3000 (FIG. 30). The expandable device 2902, however, may be made of an elastic material, although the non-elastic material is preferred.

FIG. 29 depicts the expandable device 2902 having a stop member 2910 coupled to the expandable device 2902. In one embodiment, the stop member 2910 includes a width 2912 larger than the width 2914 of the expandable device 2902 to prevent the remaining portions of the analyzer 2900 located beyond the stop member 2910 from insertion into the pelvic region of the user.

The analyzer 2900 includes the reservoir 2904 configured to temporarily retain and expel an amount of fluid from the reservoir into the tube 2906. In a preferred embodiment, the amount of fluid is a quantity of water. The use of water, as opposed to fluid, is advantageous because water is essentially incompressible, resulting in a more precise fluid flow rate measurement when compared to fluid flow rate measurements obtained with the use of fluid. In other embodiments, fluid or another gaseous matter may be used.

In one embodiment, the reservoir 2904 is a fluid dispensing bulb having a reservoir body 2916 made of a pliable material that may be pressed to expel the fluid from the reservoir 2904, i.e., the reservoir 2904 is collapsible. Said another way, the reservoir 2904 may include a squeezable reservoir body 2916 sized and shaped to fit within a palm of a user's hand, providing the user with the option to self-sufficiently expel the fluid from the reservoir 2904. In one exemplary embodiment, the amount of fluid is a maximum of 120 ml. In another embodiment, the amount of fluid is between 120 ml-300 ml for use in diagnostic testing involving greater complexity than diagnostic testing using up to 120 ml of fluid. In other embodiments, the amount of fluid may be outside of the aforementioned ranges.

In one embodiment, the tube 2906 is a flexible tube configured to retain the fluid within the tube 2906. In other embodiments, the tube 2906 may be non-flexible. The tube 2906 may or may not be expandable. In one embodiment, the tube includes a length between approximately 6-18 inches. In other embodiments, the length may be outside of this range.

FIG. 29 shows the analyzer 2900 having the fluid-flow control valve 2908 disposed between the expandable device 2902 and the reservoir 2904. In one exemplary embodiment, the fluid-flow control valve 2908 is coupled to the tube 2906. In other embodiments, the fluid-flow control valve 2908 may be coupled to other components of the pelvic region analyzer 2900 and is in no way limited to being coupled to tube 2906.

In use, the fluid-flow control valve 2908 allows the fluid to flow freely along the fluid-flow path from the reservoir 2904 to the expandable device 2902. As mentioned above, the fluid-flow control valve 2908 is also operable to provide a selectively variable level of resistance as the amount fluid passes from the expandable device to the reservoir 2904, i.e., the fluid-flow control valve 2908 is a one-way valve. The fluid-flow control valve 2908 may be a ball valve, a diaphragm valve, a needle, a butterfly valve, or the like. In one embodiment, the fluid-flow control valve 2908 is manually adjusted. In other embodiments, the fluid-flow control valve 2908 may be automatically adjusted. For example, the fluid-flow control valve 2908 may respond to signals generated by an independent device, e.g., a flow meter, the fluid flow rate reading device 1340 described above, or the fluid flow rate reading device 3000 (FIG. 30). In one exemplary embodiment, the fluid-flow control valve 2908 may be adjusted to provide a low level of resistance, a medium level of resistance, and/or a high level of resistance, in accordance with a user's pelvic muscle strength. Advantageously, the expandable device 2902, the collapsible reservoir 2904, and the tube 2906 together form a fluid flow rate tolerant sealed system. The fluid flow rate tolerant sealed system is configured to retain the fluid within the system and seal fluid flow therein. This presents a significant advantage over devices, such as devices that utilize a syringe to expel fluid, because a syringe would only hold the fluid until the components of the syringe separate and does not contain a fluid tolerant seal. Said another way, a syringe is unable to withstand significant flow conditions and would separate from the remainder of the device if exposed to flow, rendering the device inoperable for indicating and/or measuring fluid flow rate.

FIG. 30 illustrates the analyzer 2900 having the fluid flow rate reading device 3000 coupled thereto. The fluid flow rate reading device 3000 may be, without limitation, the fluid flow rate reading device 1340 and/or the fluid flow rate reading device 1370 described above. In another embodiment, the fluid flow rate reading device 3000 may be the handheld device 2500. In other embodiments, the fluid flow rate reading device 3000 may be an alternative fluid flow rate reading device, with or without the features described above. For example, the fluid flow rate reading device 3000 may or may not include an electrical connection, the user interface described above with respect to FIG. 22, the electronics architecture 2300 described with respect to FIG. 23, and/or the electronics architecture 2700 described above with respect to FIG. 27.

The fluid flow rate reading device 3000 is shown coupled to the analyzer 2900 through a fluid-flow control valve 3002. The fluid-flow control valve 3002 may have the same features as the fluid-flow control valve 2908, with the addition of a fluid flow rate port 3004 disposed on the fluid-flow control valve 3002 for coupling the fluid flow rate reading device 3000 thereto. In other embodiments, other coupling mechanisms may be used to couple the fluid flow rate reading device 3000 to the analyzer 2900.

The fluid flow rate reading device 3000 is operable to measure a fluid flow rate exerted by a user in response to the level of resistance provided by the fluid-flow control valve 3002. Such feedback advantageously allows a physician to prescribe the appropriate treatment regimens. As a further advantage, the analyzer 2900, in combination with the fluid flow rate reading device 3000, allows the user to perform strengthening of the pelvic muscles, as well as view the level of resistance and elicit biofeedback from the fluid flow rate reading device 3000.

In one exemplary embodiment, the analyzer 2900 having the fluid flow rate reading device 3000 coupled thereto, provides an indication of a muscle squeeze strength of the user in response to the selected level of resistance. In one embodiment, the indication of the muscle squeeze strength is communicated using a sensor (not shown) on the analyzer 2900. The sensor receives the indication of a muscle squeeze, i.e., squeezing of the internal and/or external sphincter as the rectum tightens. The analyzer 2900 and/or the fluid flow rate reading device 3000, may include a speaker (not shown) to emit a sound that indicates the strength of the muscle squeeze. In one exemplary embodiment, a volume of the sound increases in accordance with the strength, e.g., force, that is exerted by the muscle(s) on the sensor. In another exemplary embodiment, the analyzer 2900 and/or the fluid flow rate reading device 3000 provides an indication of a muscle endurance in response to the selected level of resistance provided by the fluid-flow control valve 3002. A duration of the sound, i.e., the time that the fluid flow rate is imparted corresponding to a contraction of the muscle, indicates endurance of the exercise.

The analyzer 2900 may be set up to perform diagnostic procedures, e.g., without limitation, an anal manometry diagnostic procedure such as that described in method 1000, a Rectal Sensation Threshold Tone and Compliance diagnostic test such as that described in method 1200, and/or a Recto-Anal Inhibitory Reflex (RAIR) diagnostic test such as that described in method 1100. Using the RAIR diagnostic test as an example, the graphing mode of the fluid flow rate reading device 3000 may be entered to measure the user's response to the rapid introduction of the fluid into and rapid withdrawal of fluid out of the expandable device 2902. Such diagnostic procedures may be performed by a physician in a hospital or other clinical setting.

Figure 31:
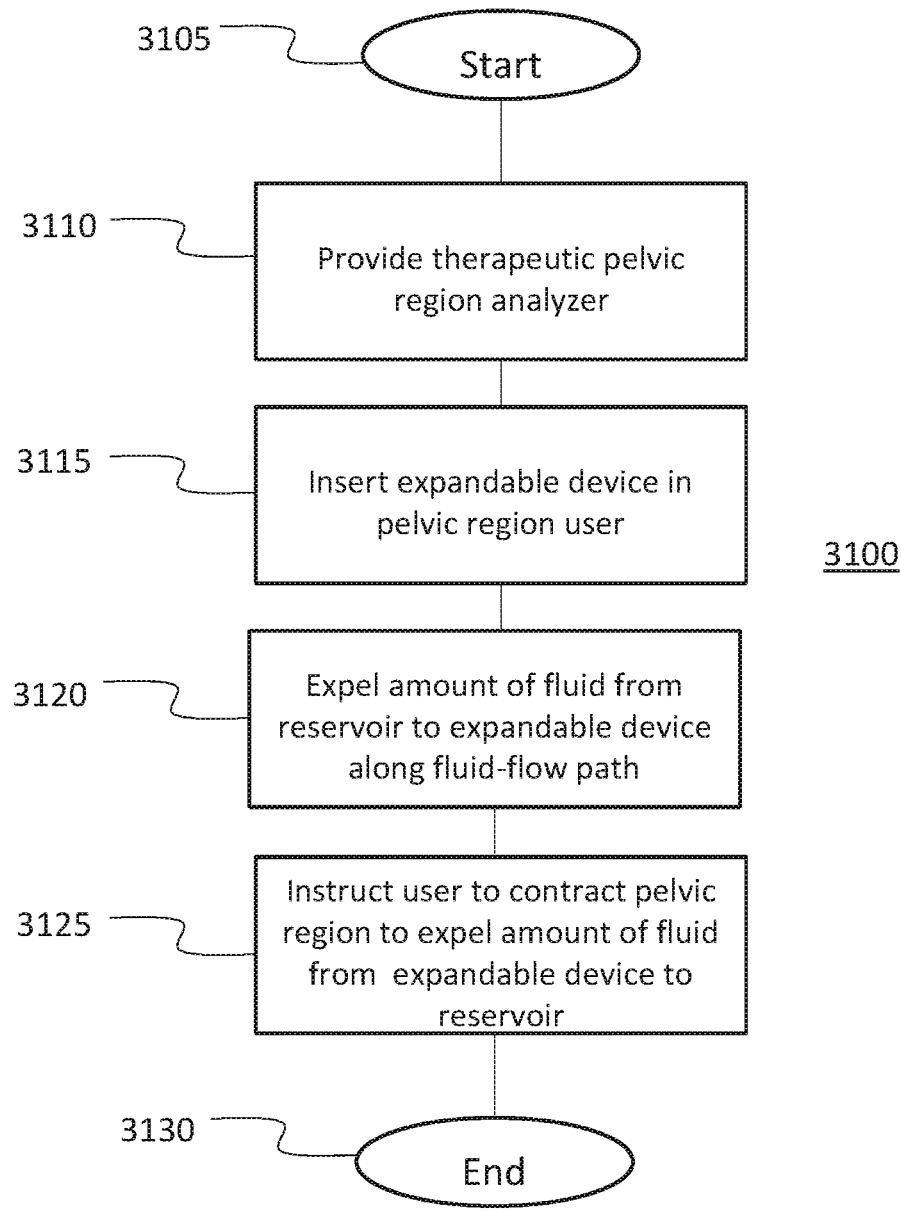
FIG. 31 is a flow diagram for an exemplary embodiment for providing pelvic region therapy according to the invention.

FIG. 31, in conjunction with FIGS. 29-30, illustrates an exemplary process-flow diagram depicting a method 3100 for providing pelvic region therapy. The steps delineated in the exemplary process-flow diagram of FIG. 31 are merely exemplary of a method 3100 for providing pelvic region therapy and said steps may be carried out in another order, with or without additional steps included therein.

In said process, the method begins at step 3105 and immediately proceeds to the step 3110 of providing, e.g., bringing into physical existence, a therapeutic pelvic region analyzer, such as the analyzer 2900 of FIG. 29. The present method however, is not limited to use with the analyzer 2900 but may also be used with other pelvic region analyzers as well. In one embodiment, the analyzer 2900 preferably, but not necessarily, includes the expandable device 2902, the reservoir 2904, the tube 2906, and the fluid-flow control valve 2908, 3002 described in detail above. The fluid flow rate reading device 3000 may be coupled to the analyzer 2900, though, for example, the fluid flow rate port 3004 disposed on the fluid-flow control valve 3002.

In step 3115, the expandable device 2902 is inserted into the pelvic region of a user. The pelvic region may be anal or vaginal. The expandable device 2902 may or may not include the stop member 2910 described above. In one embodiment, step 3115 is performed by the user. In other embodiments, step 3115 may be performed by a physician, a therapist, or another treatment provider. Prior to insertion of the expandable device 2902, the reservoir 2904 may be filled with an amount of fluid. In one embodiment, the amount of fluid includes a maximum of 120 ml of fluid. In other embodiments, the amount of fluid may be greater than 120 ml of fluid. In a preferred embodiment, the fluid is water, although other liquids, or an alternative gaseous matter be used.

In step 3120, the fluid is expelled from the reservoir 2904 to the expandable device 2902 along the fluid-flow path defined by the tube 2906. The fluid may be expelled by manually applying fluid flow rate to the reservoir 2904 or through an automatic source. In step 3125, the user is instructed to contract, i.e., squeeze, the pelvic region to expel the fluid from the expandable device 2902 in a direction toward the reservoir 2904. In a preferred embodiment, the method 3100 includes adjusting the fluid-flow control valve 2908, 3002 to provide a select level of resistance as the fluid passes from the expandable device 2902 to the reservoir 2904. Advantageously, the level of resistance may be adjusted to the comfort and strength level of the user, providing therapeutic strengthening benefits and a simple and convenient method of exercising the pelvic muscles. The fluid flow rate reading device 3000 is operable to measure a force exerted by the user in response to the select level of resistance provided by the fluid-flow control valve 3002. The fluid flow rate reading device 3000 may also be used in combination with a sensor (not shown) to provide diagnostic testing, as described in detail above. In one embodiment, the method 3100 includes repeating the step of expelling the fluid from the reservoir 2904 to the expandable device 2902 along the fluid-flow path to provide pelvic region therapy to the user. The method 3100 ends at step 3130.

The present invention provides a simplification of the learning process required for the patient participation aspect of pelvic region rehabilitation and complements an electrical stimulation part of pelvic rehabilitation. Biofeedback is provided to the patient in response to their anorectal muscle action. A standard pelvic region probe, e.g. an anal or vaginal probe, is used to indicate, for example, anal sphincter muscle response. A bright colored display may provide easy to read and interpreted analog indication of muscle response. The device may be composed of battery powered analog electrical circuitry for simplicity and high reliability. A standard medical male luer connection for common probes may also be used.

The present invention provides a handheld anorectal manometry device. Anorectal manometry measures the force of anal sphincters in order to diagnose constipation and/or anal incontinence due to certain disorders. The present invention also provides a handheld rectoanal inhibitory reflex (RAIR) and handheld rectal sensation threshold, tone diagnostic test. The rectal sensation threshold, tone diagnostic test allows measurements of patient response to graded balloon distention. In addition, the present invention provides a handheld compliance test.

The present invention provides direct measurement of anal sphincter contraction force and provides direct measure of rectal balloon fluid flow rate. The present invention can determine and display, in digital and graphical form, a rectal compliance ratio. A direct measurement of anal probe force converted for RAIR, and resting and squeeze diagnosis may be obtained using the present invention.

The present invention provides a unique probe that in one embodiment, combines an anal balloon with an anorectal probe. This unique probe is alignment insensitive. The unique probe of the present invention allows the anal balloon to be extended away from the anorectal probe for compliance diagnosis. In addition, the probe of the present invention allows the anal balloon to be seated next to the anorectal probe for RAIR diagnosis.

Diagnostic data can be stored digitally for retrieval to a device display. Diagnostic data can be downloaded to an external computer, laptop, tablet, smart phone, or other computing device via USB or wireless technologies. Data analysis and report generation can be performed on external computers, laptops, tablets, smartphones, or other computing devices. A rechargeable battery is recharged through a USB connector to a computer or wall power adapter. A multifunction display presents diagnostic data in graphical and numeric formats.

The foregoing description and accompanying drawings illustrate the principles, exemplary embodiments, and modes of operation of the disclosure. However, the disclosure should not be construed as being limited to the particular embodiments discussed above. Additional variations of the embodiments discussed above will be appreciated by those skilled in the art and the above described embodiments should be regarded as illustrative rather than restrictive. Accordingly, it should be appreciated that variations to those embodiments can be made by those skilled in the art without departing from the scope of the disclosure as defined by the following claims

What is claimed is:

1. A method for providing pelvic region therapy, the method comprising:
    providing a therapeutic pelvic region analyzer comprising:
        an expandable device sized and shaped for insertion into an opening in a pelvic region of a user;
        a reservoir fluidly coupled to the expandable device and configured to temporarily retain and expel an amount of water;
        a tube defining a fluid-flow path for the amount of water between the expandable device and the reservoir; and
        a fluid-flow control valve disposed between the expandable device and the reservoir that is a one-way valve and operable to adjust a level of resistance from a range of resistances as the amount of water passes from the expandable device to the reservoir and allow the amount of water to flow freely when the amount of water is moved from the reservoir to the expandable device while the fluid-flow control valve is set to a selected level of resistance of the range of resistances;
    providing a fluid flow rate reading device coupled to the fluid-flow control valve, the fluid flow rate reading device operable to measure a flow rate of water moved from the expandable device to the reservoir;
    inserting the expandable device in the pelvic region of the user;
    expelling the amount of water from the reservoir to the expandable device along the fluid-flow path;
    adjusting the selected level of resistance of the fluid-flow control valve to a first level of resistance of the range of resistances;
    instructing the user to contract the pelvic region to expel the amount of water from the expandable device in a direction to the reservoir;
    measuring the flow rate of water moved from the expandable device to the reservoir as a result of the user contracting the pelvic region;
    repeating the step of expelling the amount of water from the reservoir to the expandable device along the fluid-flow path, and then:
    adjusting the selected level of resistance of the fluid-flow control valve to a second level of resistance of the range of resistances;
    instructing the user to contract the pelvic region to expel the amount of water from the expandable device in the direction to the reservoir; and
    measuring the flow rate of water moved from the expandable device to the reservoir as a result of the user contracting the pelvic region with the fluid-flow control valve adjusted to the second level of resistance.

2. The method for providing pelvic region therapy according to claim 1, further comprising:
    adjusting the fluid-flow control valve to provide the second level of resistance from the range of resistances as the amount of water passes from the expandable device to the reservoir.

3. The method for providing pelvic region therapy according to claim 1, further comprising:
    providing the fluid flow rate reading device coupled to the fluid-flow control valve, the fluid flow rate reading device operable to measure a force exerted by the user at the selected level of resistance.

* * * * *